US005811310A

United States Patent [19]

Ghanbari et al.

[11] Patent Number: 5,811,310

[45] Date of Patent: Sep. 22, 1998

[54] THE ALZ-50 MONOCLONAL ANTIBODY AND DIAGNOSTIC ASSAY FOR ALZHEIMER'S DISEASE

[75] Inventors: Hossein A. Ghanbari, Lake Forest, Ill.; Peter Davies, Rye, N.Y.; Benjamin Wolozin, Columbia, Md.

[73] Assignee: Albert Einstein College of Medicine of Yeshiva Univ., Bronx, N.Y.

[21] Appl. No.: 362,783

[22] Filed: Dec. 23, 1994

Related U.S. Application Data

[63] Continuation-in-part of Ser. No. 269,640, Jul. 1, 1994, abandoned, which is a continuation of Ser. No. 116,488, Sep. 3, 1993, abandoned, which is a continuation of Ser. No. 485,149, Feb. 26, 1990, abandoned, which is a continuation-in-part of Ser. No. 100,980, Sep. 25, 1987, abandoned, which is a continuation-in-part of Ser. No. 913,494, Sep. 30, 1986, abandoned.

[51] Int. Cl.[6] .................... G01N 33/53

[52] U.S. Cl. .................... 436/518; 436/528; 436/531; 436/84; 435/70.21; 435/326; 435/7.1; 435/7.21; 435/7.92; 530/388.1

[58] Field of Search .................... 435/7.1, 7.21, 435/7.92, 7.94, 18, 21, 28, 240.27, 70.1, 70.2, 70.21, 326, 344.1; 436/518, 528, 531, 538, 540, 547, 548, 804, 811; 530/388.1

[56] References Cited

U.S. PATENT DOCUMENTS 4,486,530 12/1984 David et al. .................... 435/7.92

4,666,829 5/1987 Glenner .................... 435/6

OTHER PUBLICATIONS

Wolozin et al., Ann. Neurol 22:521–526, 1987.

Ksiezak–Reding et al, J. Biol. Chem 263(7):7943–7947, 1988.

Dickson et al, Acta Neuopathologica, 84:596–605 (1992).

Joachim et al, Journal of Neuropathology and Experimental Neuropathol. 46(6):611–622, Nov. 1987.

Davies et al, Society for Neuroscience Abstracts, 19:1636, Abstract 670.3.

Vincent et al, Society for Neuroscience Abstracts, 19:1636, Abstract 670.4.

Harlow et al, Antibodies: A Laboratory Manual, ©1988 by Cold Spring Harber Press pp. 139–243.

*Primary Examiner*—Marianne P. Allen
*Assistant Examiner*—Patricia A. Duffy
*Attorney, Agent, or Firm*—McDonnell Boehnen Hulbert & Berghoff

[57] ABSTRACT

The invention relates to an antigen associated with Alzheimer's disease and to antibodies specific for said antigen. This invention further relates to methods for diagnosing Alzheimer's disease utilizing assays containing Alzheimer's associated antigen, antibodies specific for said antigen and samples from an individual suspected of having Alzheimer's disease.

5 Claims, 24 Drawing Sheets

ALZ-50
MC-1
MC-6
MC-15
TG-4
TG-5

ALZ
NOR
3.5
3
2.5
2
1.5
1
0.5
0
-0.5
1000
500
250
125
62.5
31.25
15.63
7.813

TG5 capture, TG4 detection

PHF1 capture, TG4 detection

MC1 capture,MC15 detection

TG5 capture, MC15 detection

PHF1 capture, MCI5 detection

MC1 capture, MC2 detection

PHF1 capture, MC2 detection

MC1+TG5 capture, MC15 detection

MC1 + TG5 capture, TG4 detection

MC5 capture,MC15 detection
ALZ
NOR
2.5
2
1.5
1
0.5
0
1000
500
250
125
62.5
31.25
15.63
7.813

MC5 capture,MC15 detection

THE ALZ-50 MONOCLONAL ANTIBODY AND DIAGNOSTIC ASSAY FOR ALZHEIMER'S DISEASE

This application is a continuation-in-part of U.S. application Ser. No. 08/269,640, filed Jul. 1, 1994 now abandoned, which is a continuation of U.S. application Ser. No. 08/116,488, filed Sep. 3, 1993, now abandoned, which is a continuation of U.S. application Ser. No. 07/485,149, filed Feb. 26, 1990, now abandoned, which is a continuation-in-part of U.S. application Ser. No. 07/100,980, filed Sep. 25, 1987, now abandoned, which is a continuation-in-part of U.S. application Ser. No. 06/913,494, filed Sep. 30, 1986, now abandoned, the contents of which are all incorporated by reference herein.

FIELD OF THE INVENTION

The invention relates to an antigen associated with Alzheimer's disease, to antibodies specific for said antigen and to methods for diagnosing Alzheimer's disease utilizing said antigen and said antibodies.

BACKGROUND OF THE INVENTION

Alzheimer's disease is a progressive neurodegenerative disorder affecting 7% of the population over 65 years of age and characterized clinically by progressive loss of intellectual function and pathologically by a continuing loss of neurons from the cerebral cortex. More specifically, this pathological impairment usually is correlated with numbers of amyloid containing neuritic plaques in the neocortex and with the loss of presynaptic markers of cholinergic neurons. Neuritic plaques are composed of degenerating axons and nerve terminals, as well as possible astrocytic elements, and these plaques often exhibit a central core.

Another characteristic pathological feature of Alzheimer's disease is development of neurofibrillary tangles. A neurofibrillary tangle is an intraneuronal mass composed of paired helical filaments having unusual properties, which twist and form tangles. Neurofibrillary tangles are comprised of several different proteins.

Neurochemical studies show neurotransmitter systems are affected by Alzheimer's disease. The most consistent and severely affected system is that of the cholinergic neurons located in the Nucleus Basalis of Meynert. In addition, Alzheimer's disease causes a reduction in somatostatin, substance P and corticotropin releasing factor.

None of the above-mentioned pathologic structures, neurochemical alterations, neuritic plaques or neurofibrillary tangles are unique to Alzheimer's disease. These impairments also occur in the brains of normal aged individuals and are associated with other diseases such as Guam Parkinson Disease, Dementia Pugilistica and Progressive Supra-nuclear Palsy. For example, paired helical filaments, the twisted filaments that form the tangles and fill the neurites of plaques, also occur in certain tangles associated with other diseases such as Pick's Disease. In fact, immunologic studies have shown that epitopes of paired helical filaments exist in Pick bodies, the spherical structures found in affected neurons in the temporal cortex of brains affected by Pick's Disease. In addition, the densities of neurofibrillary tangles and neuritic plaques within the cerebral cortex of an Alzheimer's disease patient do not necessarily correlate with the stages of the illness.

Accordingly, prior hereto, the diagnosis of Alzheimer's disease has been extremely difficult. Ante-mortem diagnosis of the disease has been performed primarily by exclusion.

An article entitled, "The Neurochemistry of Alzheimer's disease and Senile Dementia", by Peter Davies in *Medicinal Research Reviews*, Vol. 3, No. 3, pp. 221–236 (1983), discusses Alzheimer's disease and at page 223 states:

> The problem in the diagnosis of Alzheimer's disease is that there is no positive test: the clinician has to rule out other causes of dementia such as strokes, microvascular disease, brain tumors, thyroid dysfunction, drug reactions, severe depression and a host of other conditions that can cause intellectual deficits in elderly people. Only when all of these problems have been eliminated as a cause of the symptoms should a diagnosis of Alzheimer's disease be accepted.

Post-mortem diagnosis of Alzheimer's disease has been based on determination of the number of neuritic plaques and tangles in brain tissue which has been stained to visualize these plaques and tangles. However, such diagnostic methods, based on neurohistopathological studies, require extensive staining and microscopic examination of several brain sections. Moreover, since the plaques and tangles also may occur in the brains of normal, elderly individuals or individuals with other diseases, a more definitive and reliable method for making the diagnosis on brain tissue is desirable.

As disclosed in U.S. Pat. No. 4,666,829 issued to Glenner et al., attempts have been made to identify the presence of an antigen specific for Alzheimer's disease. However, the antigen described by Glenner et al. is present in adults of advanced age who do not have Alzheimer's disease (see Ghanbari et al., *Journal Of The American Medical Association*, Vol. 263, pp. 2907–2910 (1990)). Therefore, a need still exists to develop a method of diagnosing Alzheimer's disease.

It is therefore an object of this invention to provide a method of diagnosing Alzheimer's disease.

It is another object of this invention to provide a method of diagnosing Alzheimer's disease utilizing cerebrospinal fluid.

It is a further object of this invention to provide an antigen which is associated for Alzheimer's disease, which antigen can be used in the diagnosis of Alzheimer's disease.

It is another object of this invention to provide antibodies which can be used in the diagnosis of Alzheimer's disease.

SUMMARY OF THE INVENTION

This invention is directed to antibodies specific for Alzheimer's disease-associated antigen, which antigen is present in individuals with Alzheimer's disease and substantially absent from individuals who do not have Alzheimer's disease. The present invention provides a specific, sensitive and simple sandwich immunoassay for diagnosis of Alzheimer's disease. The methods of the invention overcome the drawbacks of the prior art which require a diagnosis based on a process of elimination of other disorders.

Thus, this invention is directed to an Alzheimer's disease antigen present in individuals with Alzheimer's disease and substantially absent from individuals who do not have Alzheimer's disease. The antigen of the invention is comprised of several proteins and some of which have a molecular weight of about 68,000 daltons.

In addition, this invention is directed to a partially purified preparation of antigen which is a diagnostic marker for Alzheimer's disease. The antigen of the invention has an isoelectric point of about 6 in reduced or non-reduced form, binds to an affi-blue column, is at least fifty percent soluble in a solution of 0.01M sodium phosphate, 0.14M sodium chloride and 1 mM phenyl methyl sulfonyl flouride at pH 6.8, and precipitates in fifty percent saturated ammonium sulfate at 4° C.

Alzheimer antigen is detectable in cerebrospinal fluid from Alzheimer patients by western blot analysis but absent from cerebrospinal fluid from nondemented patients. In the methods described herein, 3.5 ml of cerebrospinal fluid is utilized; however, this volume could be readily reduced. Fluid volumes of from about 0.1 to 10 ml of fluid can be employed in the methods of the invention.

This invention is further directed to a method for determining the presence of antigen specific to Alzheimer's disease in a sample comprising the steps of contacting a sample with a first antibody specific for a first antigenic determinant being a complex of proteins containg a 68,000 dalton antigen and related proteins found in individuals having Alzheimer's disease such that a first antibody-antigen complex is formed; separating the first complex from the sample; contacting the first complex with at least one second antibody specific for a second antigenic determinant on said Alzheimer's antigen, wherein said second antigenic determinant may be the same as said first antigenic determinant, such that said second antibody binds to the first complex to produce a second complex; and detecting the presence of the second complex, the presence of said second complex indicating the presence of antigen specific to Alzheimer's disease in the sample.

This invention is additionally directed to use of the above-described method for diagnosing Alzheimer's disease using pre-mortem or post-mortem brain tissue or cerebrospinal fluid from an individual as a sample, and utilizing the Alzheimer's disease antigen and antibodies of the invention. The samples from the patient include, in addition to brain tissue or cerebrospinal fluid, other tissues, blood, urine, and serum.

This invention is further directed to a method for detecting and measuring the amount of antigen specific to Alzheimer's disease in a sample comprising the steps of contacting a sample with a first antibody specific for a first antigenic determinant on a protein complex containing the 68,000 dalton antigen found in individuals having Alzheimer's disease such that a first antibody-antigen complex is formed; separating the resulting complex from the sample; contacting the complex with a detectable second antibody specific for a second antigenic determinant on the protein complex containing the 68,000 antigen, wherein said second antigenic determinant may be the same as said first antigenic determinant such that said second antibody binds to the first complex; and detecting and measuring the amount of said second antibody bound to the complex.

Previous attempts have been made to design a diagnostic test for Alzheimer's disease based on detecting paired helical filament immunoreactivity in cerebrospinal fluid by ELISA. These tests have proved to be of limited diagnostic value because of the overlap between Alzheimer samples and nondemented control samples. Use of a western blot analysis protocol for detection of Alzheimer antigen obviates much of this difficulty. The data presented herein indicates that cerebrospinal fluid detection of Alzheimer antigen can distinguish between Alzheimer's samples and nondemented control samples. The quantitative data presented also shows that detection of Alzheimer antigen in cerebrospinal fluid can distinguish between Alzheimer's disease and other dementing illnesses such as Pick's Disease, multi-infarct dementia or Huntington's Disease because of the selective and quantitative accumulation of Alzheimer antigen in Alzheimer's disease.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

Figure 1:
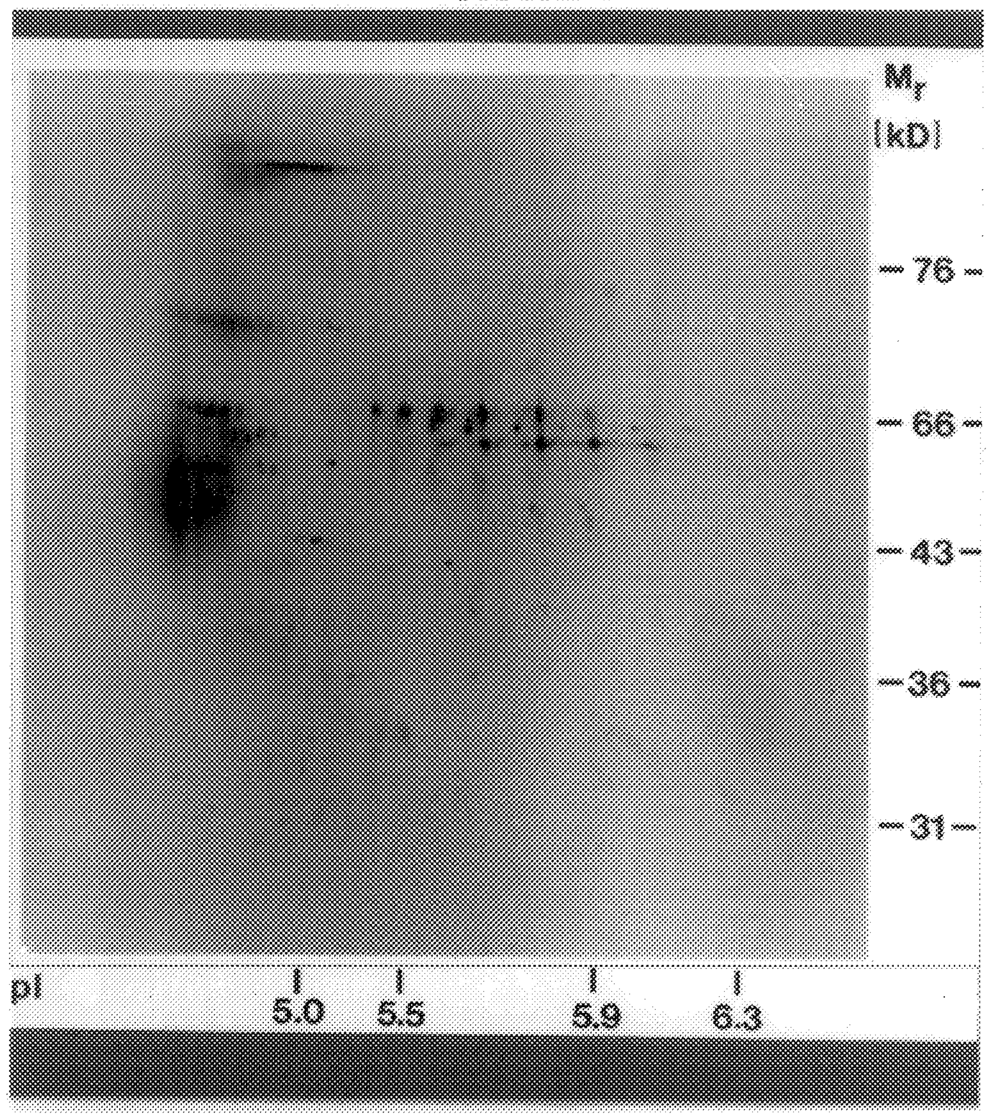
FIG. 1 represents a two dimensional gel of the Alzheimer's antigen of the invention.

By "individuals with Alzheimer's disease" is meant individuals or patients suffering from, affected by, or manifesting the clinical symptoms of the disease.

The various terms used herein to describe the pathological lesions associated with Alzheimer's Disease are defined as follows. Large fibrous inclusions found in certain affected neurons in Alzheimer's Disease are termed "Neurofibrillary Tangles" (NFTs). These structures are composed largely of arrays of tightly packed paired helical filaments (PHFs) containing Alzheimer's antigen but numerous other protein species are also present in these structures. This NFT form of PHF is highly insoluble in solvent conditions used to isolate the soluble Alzheimer's antigen of the invention. Soluble Alzheimer's antigen derives largely from abnormal neurites (sometimes referred to as "neuropil threads"). These abnormal neurites comprise the predominent pathology in Alzheimer's Disease. In fact, it has been estimated that as much as 90% of the Alzheimer antigen in the cortex of the average Alzheimer case is present in neuronal processes (abnormal neurites) rather than in the plaque or tangle (Wolozin, Ann. Neurol. 22: 521–526, 1987).

The other abnormal lesions found in Alzheimer brain are the amyloid plaques, sometimes referred to as "senile plaques". Senile plaques are actually two distinct types of structures, the classical plaques described by Alzheimer that is composed of degenerating neuronal elements (dystrophic neurites) surrounding a central core of amyloid, and the "diffuse" or "primitive" plaques consisting of deposits of amyloid without the halo of degenerating neurites (Tagliavini et al., Neurosci. Lett. 93: 191–196, 1988; Dickson et al., Am. J. Path. 132: 86–101, 1988). Plaques containing degenerating neurites are now referred to as "neuritic plaques". The degenerating neurites in these structures contain Alzheimer antigen and stain with the antibodies of the invention. Primitive or diffuse plaques do not contain Alzheimer antigen nor do they immunostain with the antibodies of the invention. Diffuse plaques can be found in large numbers in the brains of the majority of the very elderly (over 80 years), and are only rarely associated with dementia when present without evidence of degenerating neurites (Davies et al., Neurology 38: 1688–1693, 1988; Delkaere et al., Neurosci. Lett. 116: 87–93, 1990; Dickson et al., Neurobiol. Aging 13: 179–189, 1991).

The antigen described herein as being discovered in the brains and cerebrospinal fluid (CSF) of Alzheimer patients is referred to herein as the "Alzheimer antigen" regardless of where it is found in a person if the antigen has the properties set forth herein. It has been discovered that one such Alzheimer antigen is a protein so that the Alzheimer antigen is also referred to herein as an "Alzheimer protein" when the protein property is a prominent factor in the discussion. The antibodies which are immunologically reactive with the Alzheimer antigen are referred to herein as "Alzheimer antibodies."

The invention provides antibodies capable of substantial immunoreactivity with an antigen present in elevated amounts specific to Alzheimer patients, i.e., Alzheimer antibody. The invention is also the use of Alzheimer antibody to diagnose Alzheimer's disease. According to one aspect of the invention, the Alzheimer antigen is a protein complex with a major species having an apparent molecular weight of about 68,000 daltons and is found in Alzheimer patients while being present in much reduced quantities in non-Alzheimer patients, including patients suffering from other neurologic diseases.

In the instant invention, a method is provided for determining the presence of elevated levels of an antigen specific to Alzheimer's disease in a sample, thereby diagnosing Alzheimer's disease. The method comprises contacting a sample from an individual suspected of having Alzheimer's disease with a first antibody specific for an antigenic determinant on the Alzheimer's antigen and capable of binding to the antigen so as to produce a first complex. The resulting first complex then is separated and recovered from the sample and contacted with at least one second antibody specific for a second antigenic determinant on the antigen. The second antigenic determinant may be the same as the first antigenic determinant due to the multiepitopic nature of the antigenic entity. The second antibody is capable of binding to the antigen present in the first complex such that when the second antibody binds the antigen, a second complex is formed, which consists of antigen bound to the first and second antibodies. The presence of the second complex is detected and, thereby, the presence and/or level of the antigen specific to Alzheimer's disease in the sample is determined and, optionally, quantitated.

The sample used in the assay of the invention is preferably selected from the group consisting of brain tissue, pre or post-mortem, cerebrospinal fluid, urine and blood. In a preferred embodiment, the sample comprises cerebrospinal fluid.

In a further preferred embodiment, both the first and second antibodies are monoclonal antibodies. A preferred monoclonal antibody of the invention is ALZ-50 secreted by hybridoma No. HB9205, which was deposited under the Budapest Treaty on Sep. 17, 1986 with the American Type Culture Collection, Rockville, Md. Viability was confirmed on Sep. 24, 1986.

ALZ-50 has become the standard reagent for detecting the presence of Alzheimer's disease in this field. (See, for example, Wood et al., *Histochemical Journal*, Vol. 21, No. 11, pp. 659–662 (1989); Itagaki et al., *Annals of Neurology*, Vol. 26, No. 5, pp.685–689 (1989); Beach et al., *Brain Research*, Vol. 501, No. 1, pp. 171–175 (1989); Love et al., *Journal of Neuropathology and Experimental Neurology*, Vol. 47, No. 4, pp. 393–405 (1988); Nukina et al., *Neuroscience Letters*, Vol. 87, No. 3, pp. 240–246 (1988); and Hyman et al., *Brain Research*, Vol. 450, pp. 392–397 (1988).)

The antigen of the invention which is associated with Alzheimer's disease (the Alzheimer's antigen) is an aggregate of several proteins (see FIG. 1) and the major protein species have an apparent molecular weight of about 68,000 daltons on a reducing SDS gel. Since its first description, the Alzheimer's antigen has been additionally referred to as A68, tau, hyperphosphorylated tau (Lee et al., Science 251: 675–678, 1991), abnormally phosphorylated tau (Grundke-Iqbal et al., Proc. Natl. Acad. Sci. 83: 4913–4917, 1986), soluble PHF (Greenberg and Davies, Proc. Natl. Acad. Sci. 87: 5827–5831, 1990), PHF tau (Greenberg et al., J. Biol. Chem. 267: 564–569, 1992), and Alzheimer's Disease Associated Protein (ADAP) (Ghanbari et al., JAMA 263: 2907–2910, 1990). All terms are deemed to be equivalent when referring to the Alzheimer's antigen herein. It contains tau and phosphorylated tau. This antigen can be used to raise monoclonal antibodies which can be used in a diagnostic assay for Alzheimer's disease.

In the diagnostic assays of the invention, the first antibody can be attached to a suitable solid matrix, such as, for example polystyrene beads. A sample is obtained and contacted with a suitable amount of first antibody to produce a first complex. The contact preferably involves adding the sample to a column of polystyrene beads coated with the first antibody.

The complex which results from contacting the sample with the first antibody is separated from the sample by elution methods known to those skilled in the art.

The separated first complex is contacted with at least one second antibody specific for an antigenic determinant on the antigen and capable of binding to the antigen in the complex. The antigenic determinant to which the second antibody is directed may be the same one as that to which the first antibody is directed due to the multiepitopic nature (i.e. repeating epitopes) of the antigenic entity. The conditions for effecting such contact are described herein and known to those skilled in the art.

The first or second antibody of the methods of the present invention may be made detectable by attaching an identifiable label thereto. In a preferred embodiment, the second antibody is made detectable. The antibody preferably is made detectable by attaching to it an enzyme conjugated to an appropriate substrate which, in turn, catalyzes a detectable reaction. The enzyme may be horseradish peroxidase, beta-galactosidase or alkaline phosphatase. Other means of detection of the antibody include attaching a fluorescent or radiolabel thereto. Alternatively, the antibody may be detected by use of another antibody directed to it, the other antibody being labeled or having an enzyme substrate bound to it.

The presence of the detectable antibody bound to the antigen of the complex consisting of antigen bound to the first and second antibody may be readily detected using well-known techniques. Thus, if the detectable antibody is linked to an enzyme conjugated to an appropriate substrate, the optical density of the detectable bound antibody is determined using a quantum spectrophotometer. If the detectable antibody is fluorescently labeled, the fluorescent emission may be measured or detected using a fluorometer technique. In a similar manner, if the detectable antibody is radioactively labeled, the bound antibody may be detected using a radioactivity detection techniques. By comparing the results obtained using the above-described methods on the test sample with those obtained using the methods on a control sample, the presence of the antigen specific to Alzheimer's disease may be determined. The elevated amount of antigen specific to Alzheimer's disease is thereby detected and may optionally be quantitated.

In this method for detecting and measuring Alzheimer's disease antigen, the first and second antibody may be monoclonal antibodies. Alternatively, the first or the second detectable antibody can be a polyclonal antibody.

The methods for qualitatively or quantitatively determining the Alzheimer's disease antigen may be used in the diagnosis of Alzheimer's disease. Utilization of the methods of the present invention is advantageous over prior art methods because the present invention provides simple, sensitive, very specific methods for detecting Alzheimer's antigen. The Alzheimer's antigen is well-suited for sandwich immunoassay since it is present in aggregate form and, hence, is multiepitopic. This is in contrast to cross-reactive proteins, which are soluble and usually contain one epitope per antibody. Moreover, the assay is linear up to 0.5 absorbance unit (r=0.9), reproducible (CV less than 10%), sensitive, and specific. With preformulated reagents and standard supplies, the assay is simple and rapid. 120 data points can be readily generated in about 4 hours.

The methods described herein for use with cerebrospinal fluid are applicable to blood and urine. The following is another test procedure believed to be suitable for detecting the presence of Alzheimer antigen in the blood or other body fluids of a person having Alzheimer's disease. The procedure is similar to the procedure used in the detection of HTLV-III as disclosed in "Immunoassay for the Detection and Quantitation of Infectious Human Retrovirus, Lymphadenopathy-Associated Virus (LAV)", by J. S. McDougal et al., *Journal of Immunological Methods*, Vol. 76, pp. 171–183 (1985).

In one preferred embodiment of the invention the Alzheimer antibody is of the IgM class, however, Alzheimer antibodies of the IgG class have been created and are specifically included in the term Alzheimer antibody. Using the methods described by Spira et al in an article entitled "The Identification of Monoclonal Class Switch Varients by Sib Selection and an ELISA Assay" in *Journal of Immunological Methods*, Vol. 74, pp. 307–315 (1984), Alzheimer antibodies of the IgM class were used to generate Alzheimer antibodies of the $IgG_1$ class.

Tests performed utilizing the Alzheimer antibodies of the $IgG_1$ class showed substantial reductions in non-specific binding as compared to Alzheimer antibodies of the IgM class. In general, IgM antibodies display more non-specific binding than do IgG antibodies. Alzheimer antibodies of the $IgG_1$ class from two hybridomas were compared to IgM Alzheimer antibody using homogenates of three Alzheimer brains and three normal brains. One of the $IgG_1$ Alzheimer antibodies showed much less binding to normal brain tissue than the IgM Alzheimer antibody. The other $IgG_1$ Alzheimer antibody showed no significant reactivity with the normal tissue.

Another advantage of the invention is the use of the Alzheimer antibody to carry a label, such as a radioactive label or the like to portions of the brain which are stained by the Alzheimer antibody. Thereafter a "map" of the brain can be made from the label using known methods in order to provide additional information on the brain. Generally, a conventional method is used so that the Alzheimer antibody can be combined with a suitable label so that the Alzheimer antibody acts as a carrier. The combined Alzheimer antibody and label are introduced into the brain using conventional techniques. The Alzheimer antibody attaches the label to sites of Alzheimer antigen. Thereafter, a map of the brain is made using conventional methods, thereby showing the presence and distribution of Alzheimer antigen.

The invention is illustrated further by the following examples which are not to be construed as limiting the invention in scope or spirit to the specific compounds or procedures described in them.

EXAMPLE 1

Preparation of Antibodies

1. ALZ-50

The production of monoclonal antibodies is well-known in the art and has been described in many articles including "High Frequencies of Antigen-Specific Hybridomas; Dependent on Immunization Perimeters and Prediction by Spleen Cell Analysis", by Christian Stahli et al., *Journal of Immunological Methods*, Vol. 32, pp. 297–304 (1980) and "Production of Monoclonal Antibodies; Strategy and Techniques" by S. Fazekas de St. Groth and Dolores Scheidegger, *Journal of Immunization Methods*, Vol. 35, pp. 1–21 (1983). Furthermore, descriptions of procedures and critical steps are readily available from companies such as Microbiological Associates engaged in the business of supplying related products.

The procedure used included the production of monoclonal antibodies to homogenates of ventral forebrain tissue taken during autopsies of four patients with Alzheimer's disease. The resulting antibodies were screened on the basis of their ability to differentiate brain tissue from Alzheimer patients from tissue from normal patients in both immunochemical and immunocytochemical prodecures.

The resulting monoclonal antibodies are initially assayed according to their ability to bind to Alzheimer brain homogenate using a known technique referred to in the prior art as enzyme linked immunosorbent assay (ELISA). Antibodies showing greater than a fifty percent increase or decrease in binding to homogenates of Alzheimer's brain relative to normal tissue are studied further. One particular antibody was found to be highly selective for brain tissue from Alheimer patients. This antibody, hereinafter ALZ-50 antibody, ALZ-50, is deposited with the American Type Culture Collection, Rockville, Md. as ATCC No. under deposit No. HB9205. This monoclonal antibody binds to the region on Tau shown in Table A below. ALZ-50 does not cross-react with proteins found in normal tissue under the specific assay conditions described herein.

2. Other Antibodies

The ALZ-50 monoclonal antibody described above in part 1 of this example was used to produce other antibodies specific for the Alzheimer's antigen of the invention. This was done by immunoaffinity chromatography. Large quantities of antigen were prepared from brain tissues from cases of Alzheimer's disease using AlZ-50 antibody. This material was used to immunize mice, and the spleens from these mice were used to produce new cell lines producing monoclonal antibodies reactive with the Alzheimer's antigen.

In order to purify the Alzheimer's disease antigen, cultures of the AlZ-50 cell line were screened to isolate IgG1 secreting variants. These class-switch variants arose spontaneously in cultures of IgM secreting cells. One variant was designated P42, and was shown to retain the AlZ-50 binding properties using ELISA, Western blotting and immunocytochemistry. The P42 IgG1 was purified by chromatography on protein A columns, and attached to Affi-gel 10 (Biorad Laboratories) following the manufacturer's protocol. Columns were prepared on the P42 Affi-gel 10. Extracts of brain tissue from cases of Alzheimer's disease were prepared by a single centrifugation at 27,000 g of brain homogenates. The supernatant fraction was loaded onto the P42 column, and the column was washed after loading. Bound antigens were eluted with a solution of 3M potassium thiocyanate, and the eluate was dialysed against Tris-buffered saline.

Mice were then immunized with antigen purified on the P42 column by intraperitoneal injection of 10 to 20 micrograms of protein per mouse per injection. Mice were immunized 4 or 5 times before removal of spleens for the production of hybridoma cells by standard protocols. Hybridomas were tested for the production of specific antibodies by ELISA and immunocytochemistry. Hybridomas secreting monoclonal antibodies having the basic property of selective reactivity with brain tissue from cases of Alzheimer's disease by ELISA, Western blotting and immunocytochemistry were obtained.

Figure 6:
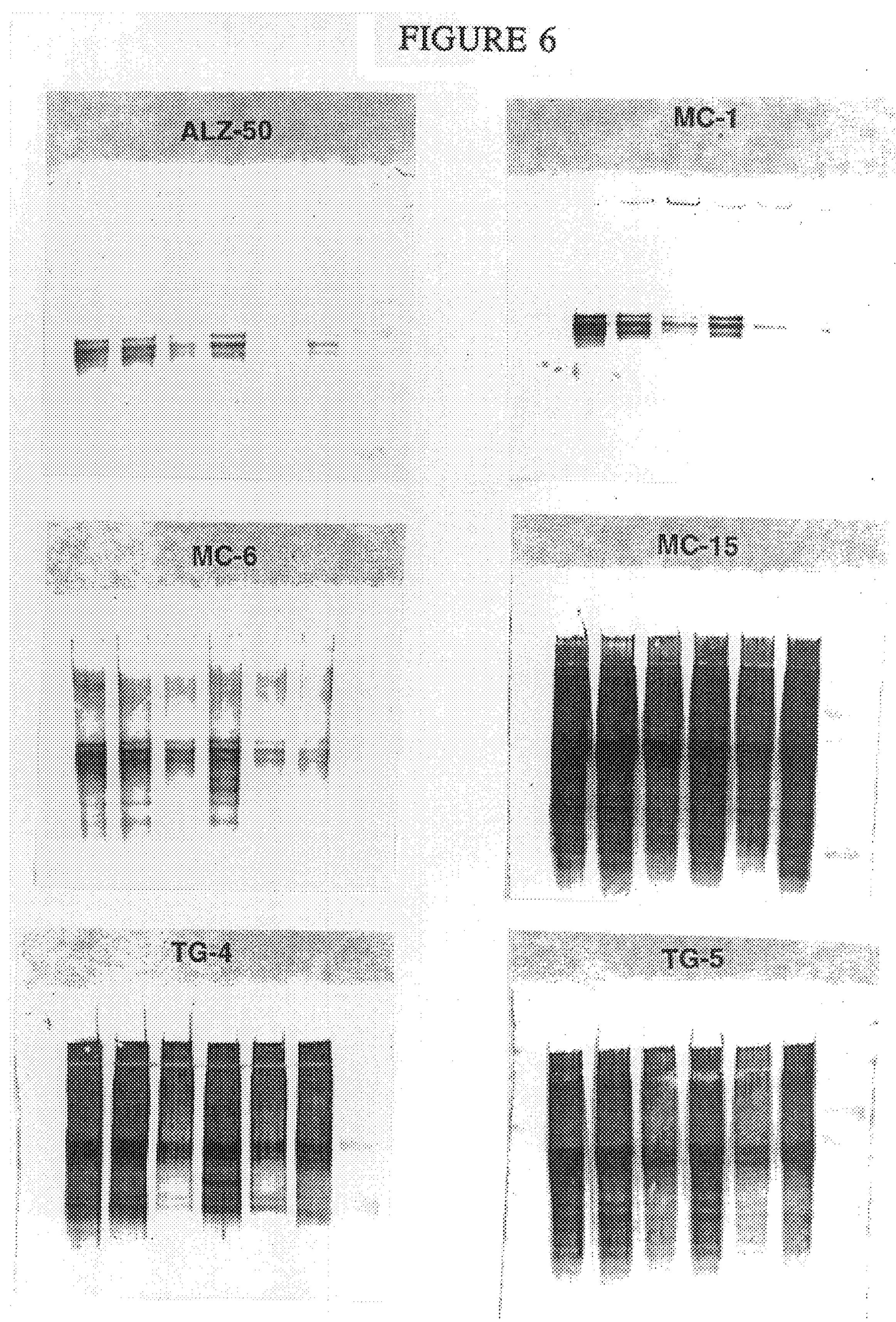
FIG. 6(A–F) represents the immunoreactivity of various monoclonal antibodies of the invention to the Alzheimer's antigen.
Figure 7A:
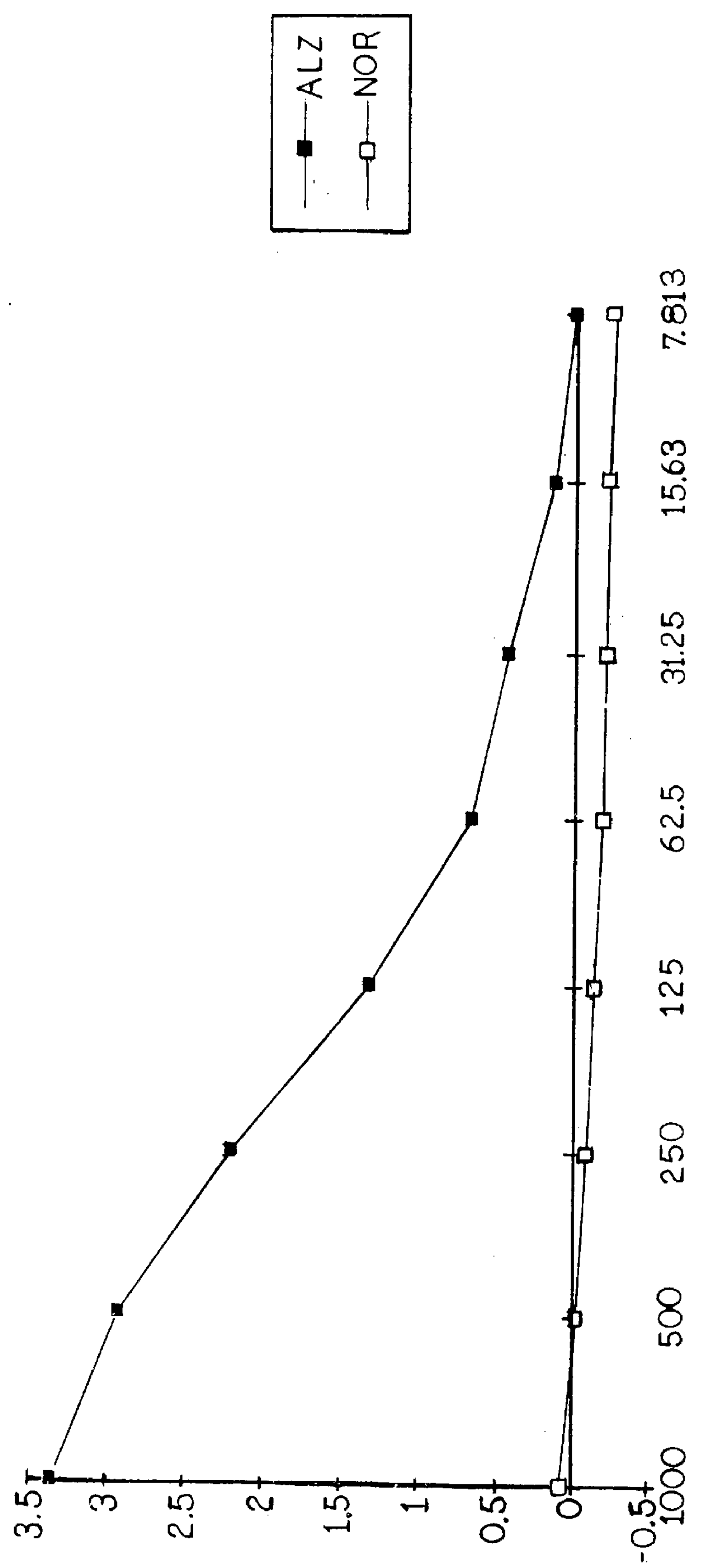
FIGS. 7A–7M represent cerebrospinal fluid assays for the Alzheimer's antigen utilizing various monoclonal antibodies, wherein one monoclonal antibody is used to capture the antigen and the second monoclonal antibody is used for detection purposes.
Figure 7B:
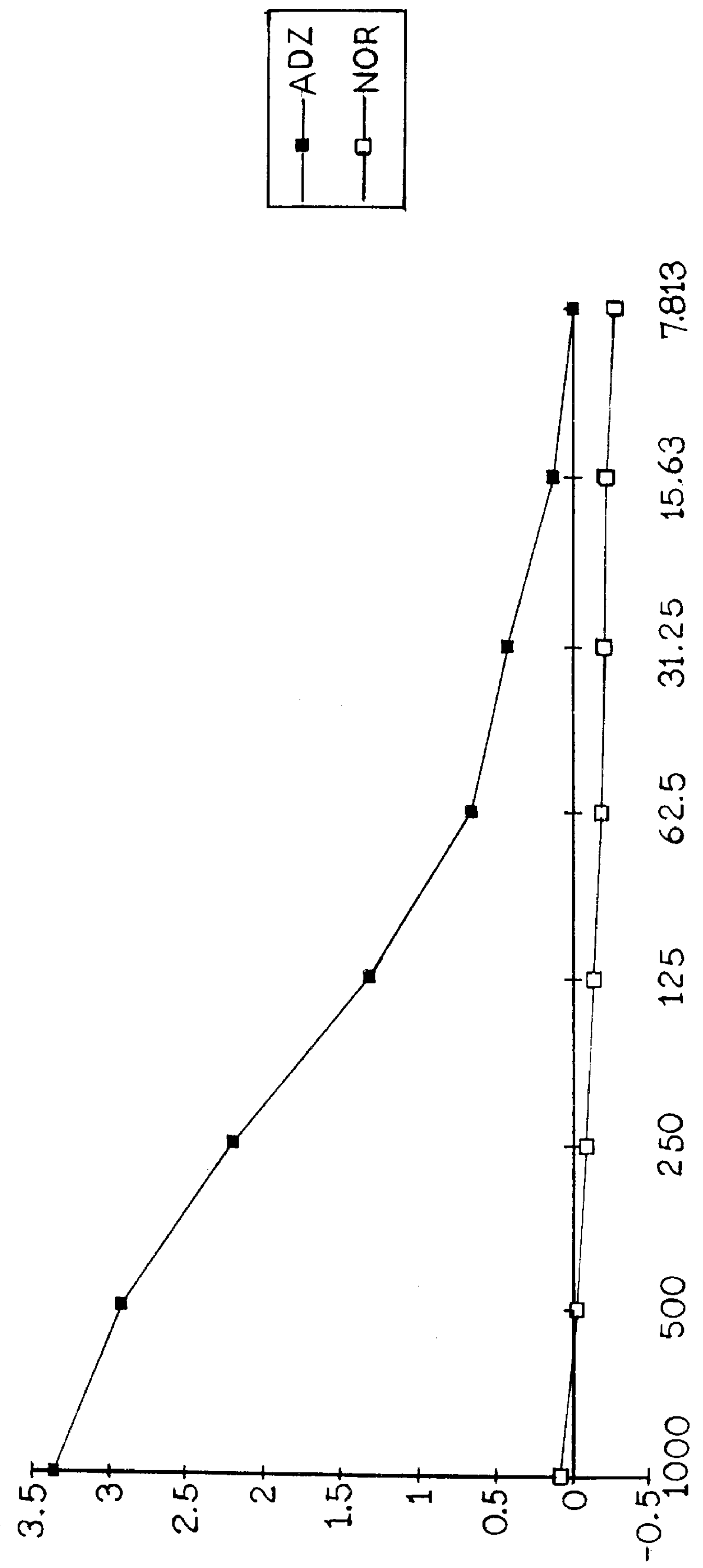
Figure 7C:
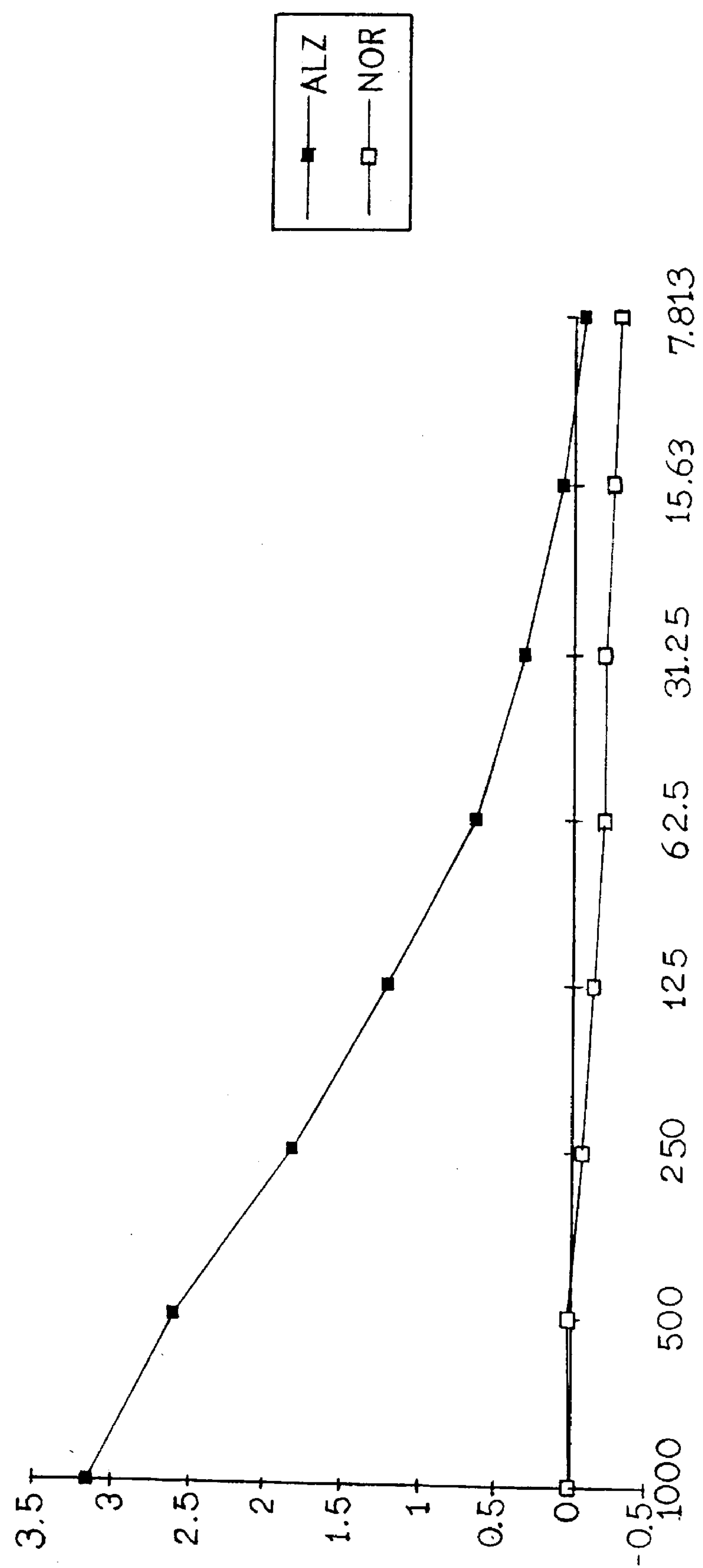
Figure 7D:
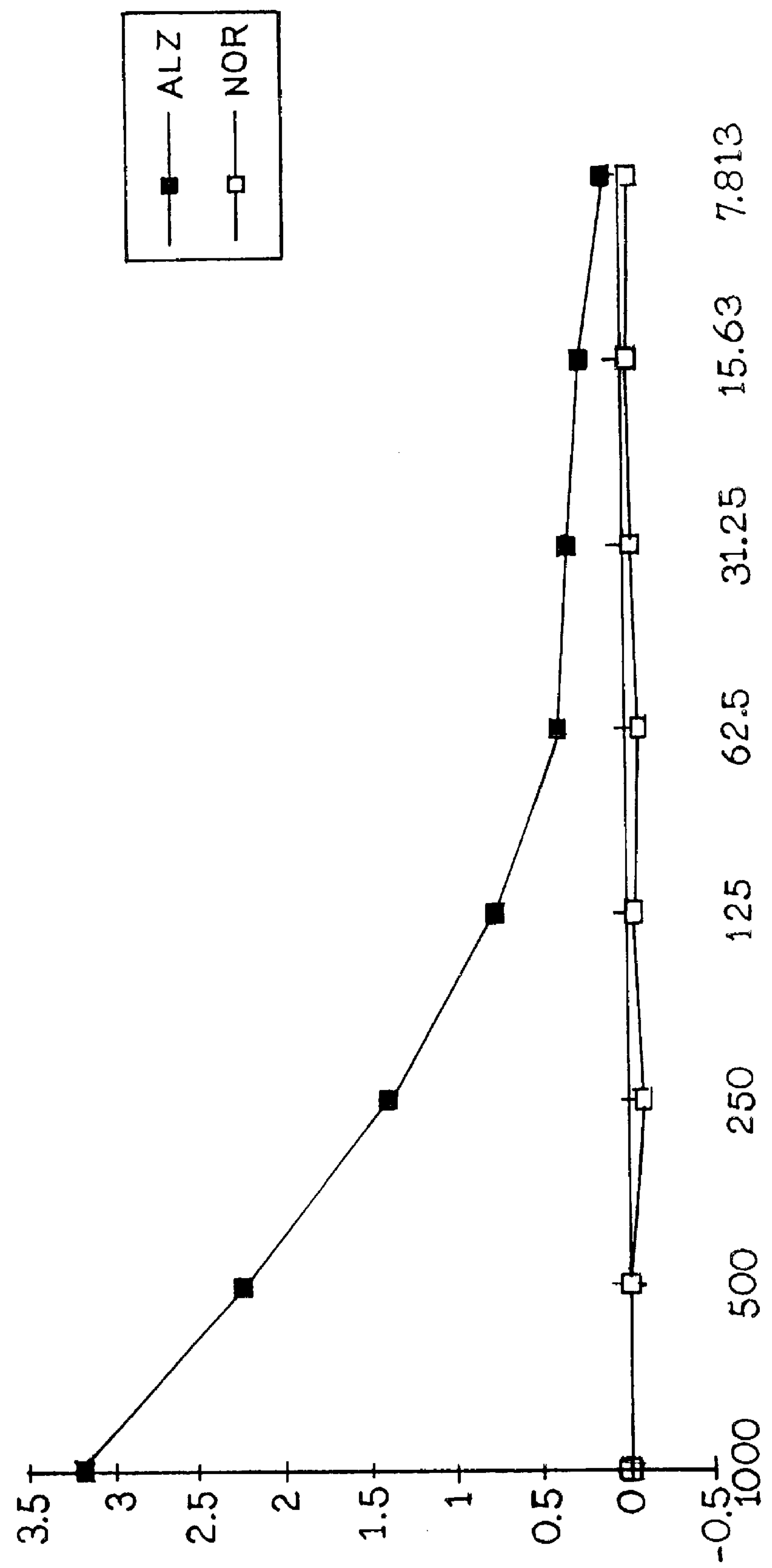
Figure 7E:
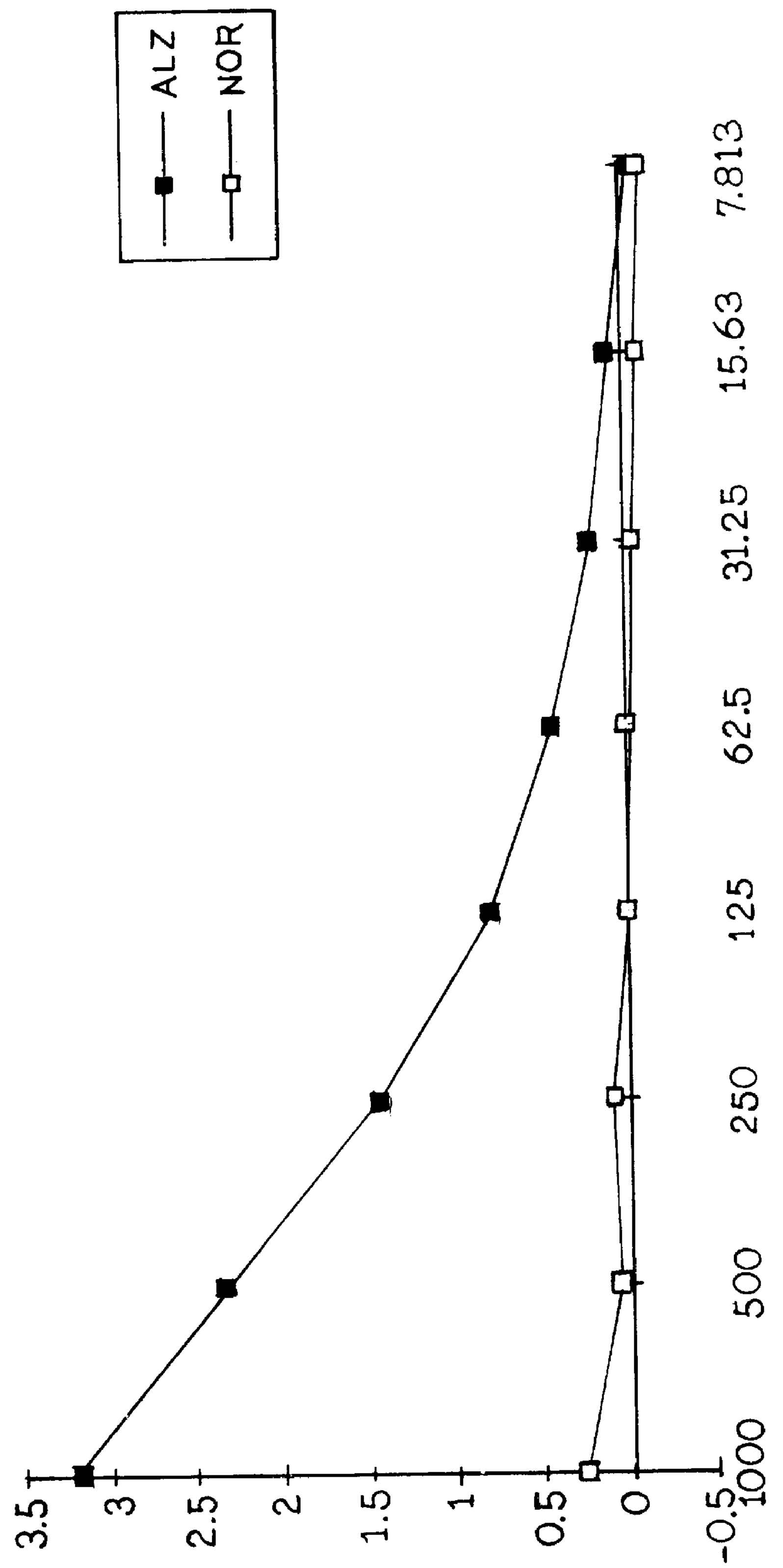
Figure 7F:
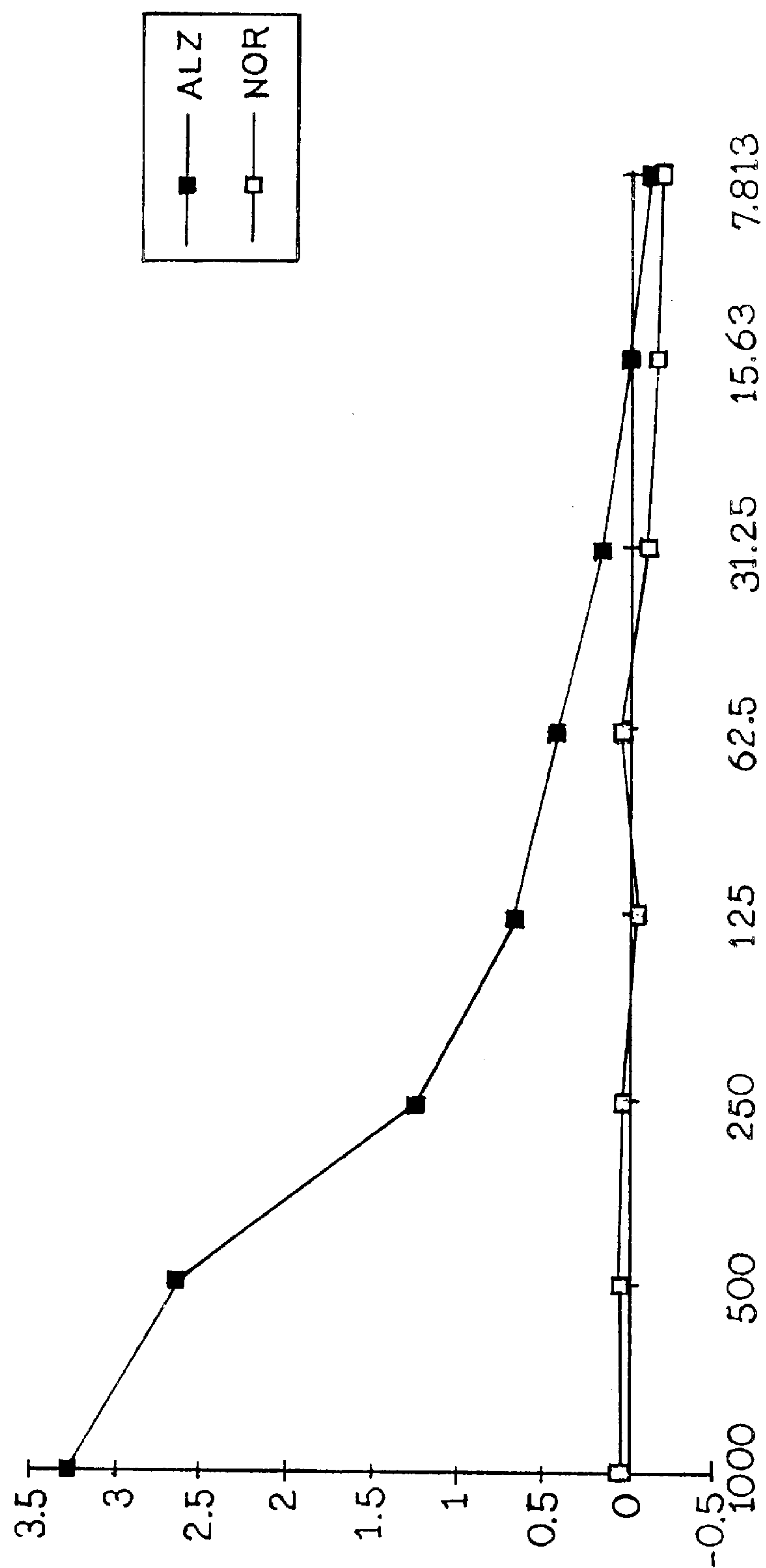
Figure 7G:
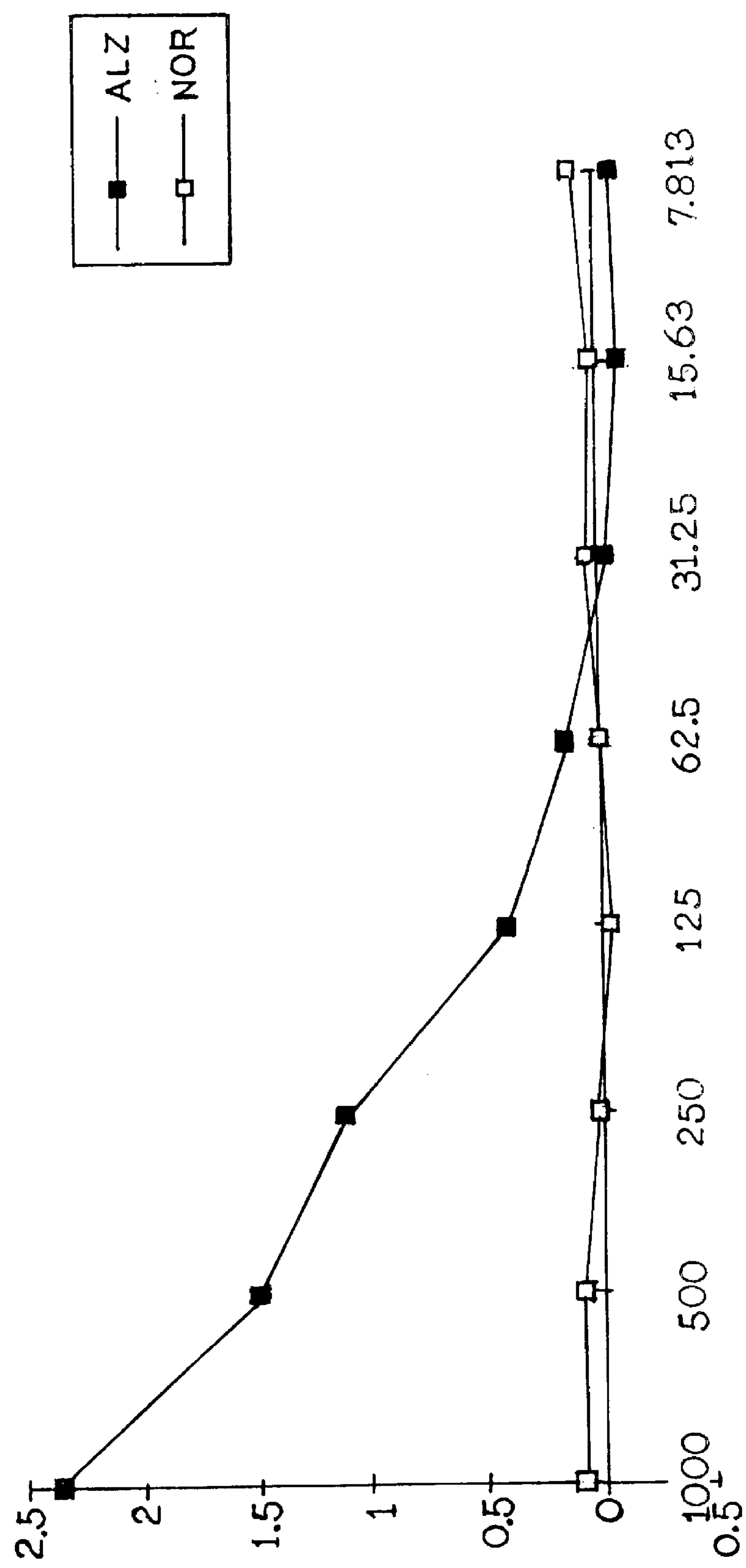
Figure 7H:
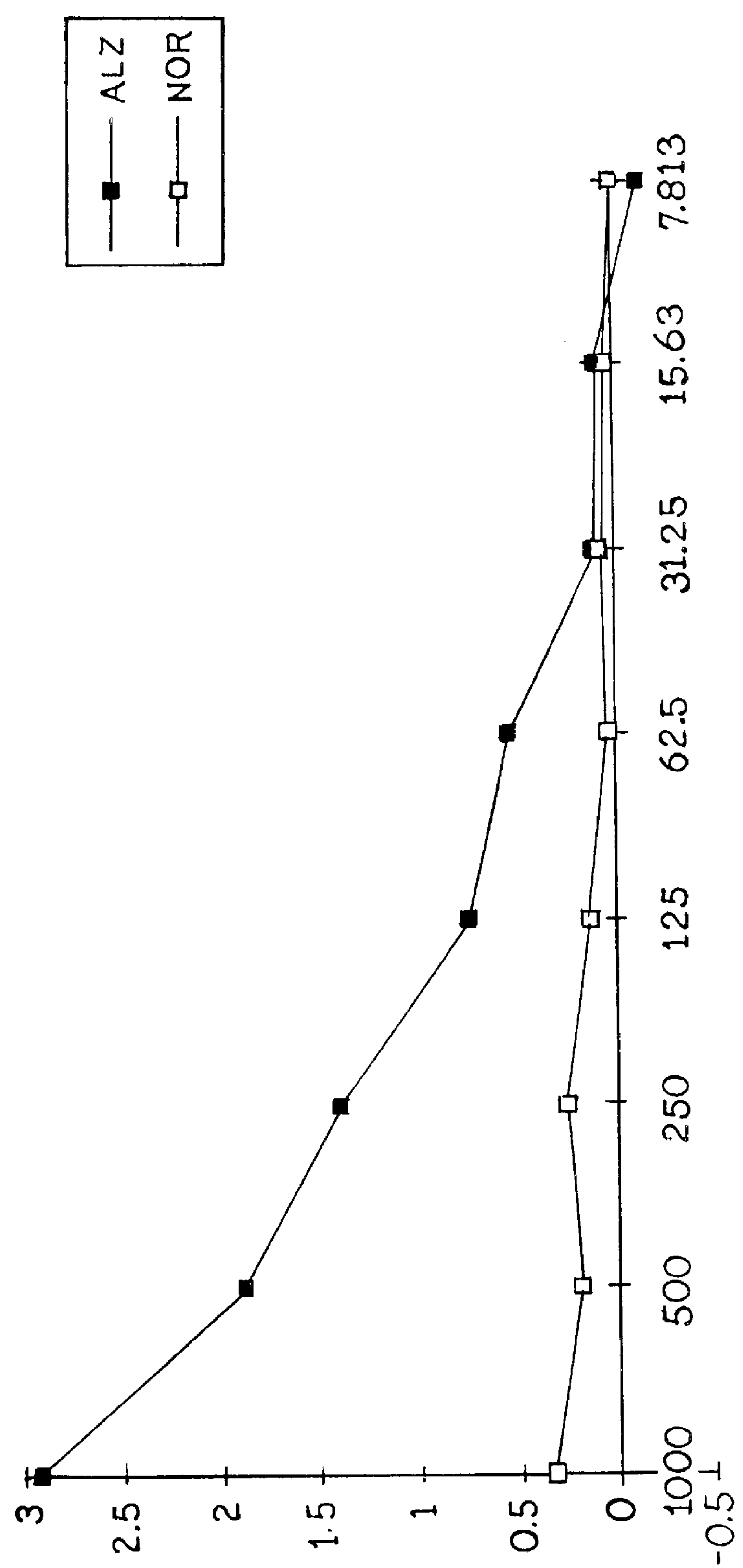
Figure 7I:
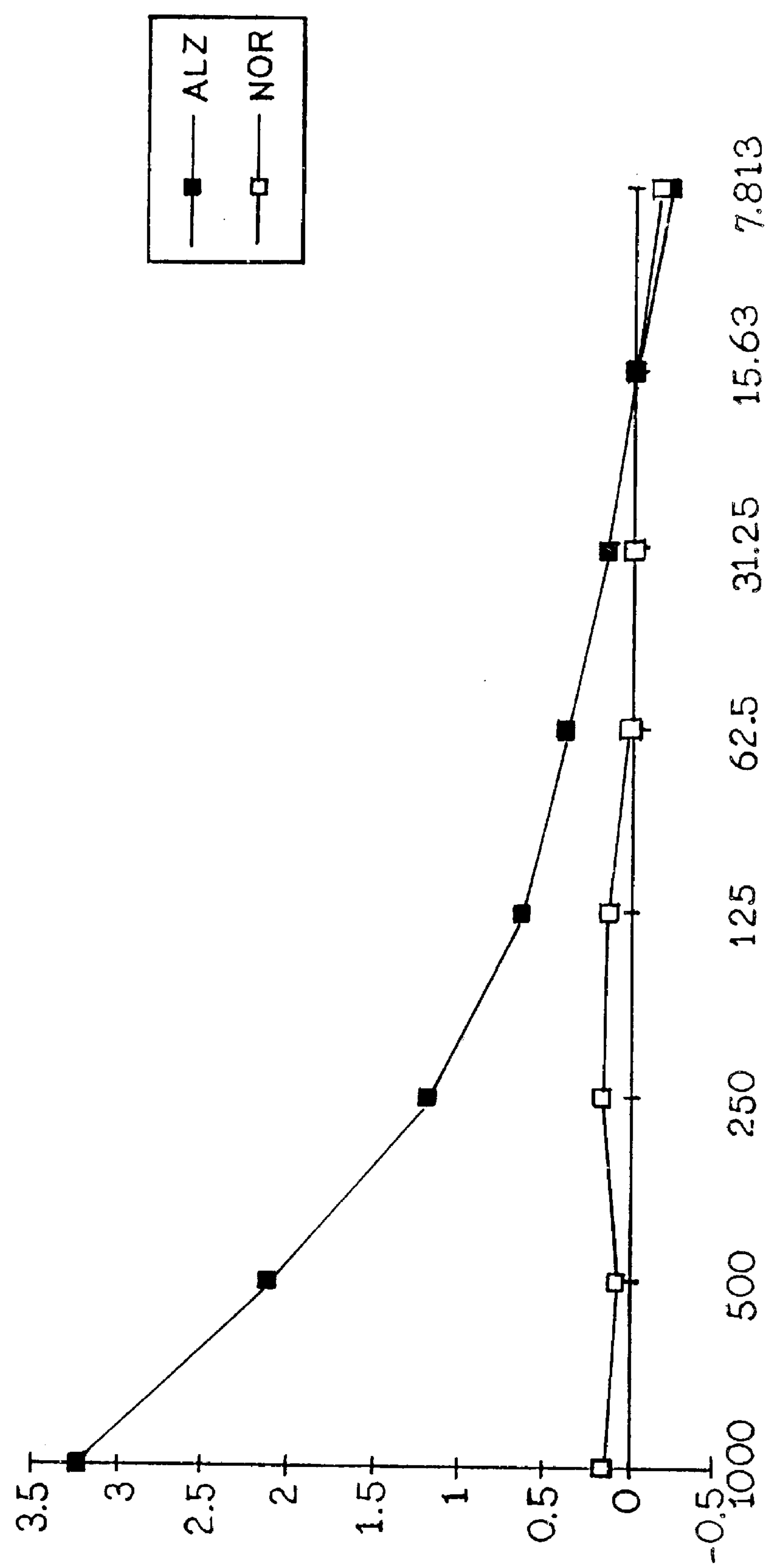
Figure 7J:
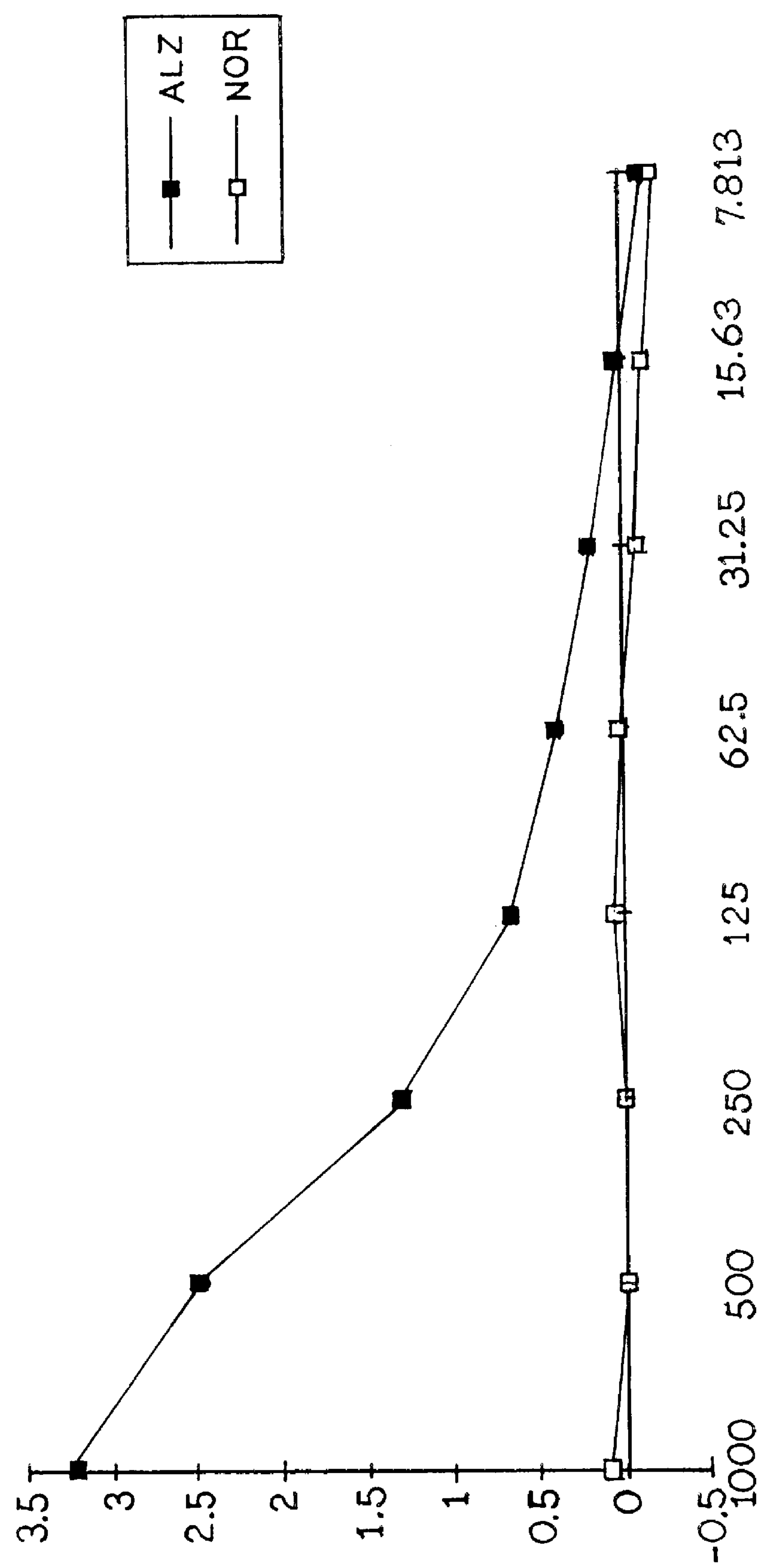
Figure 7K:
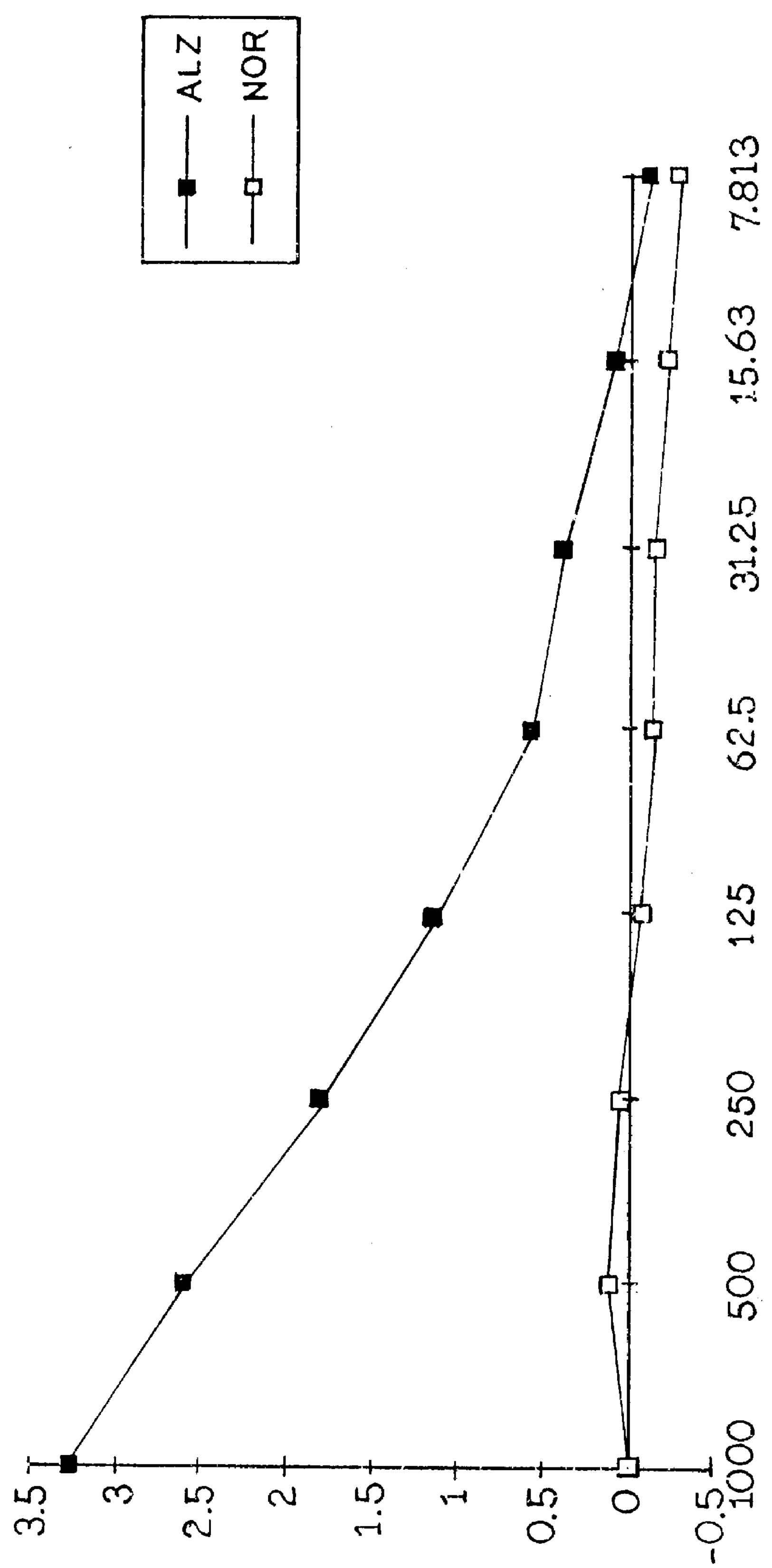
Figure 7L:
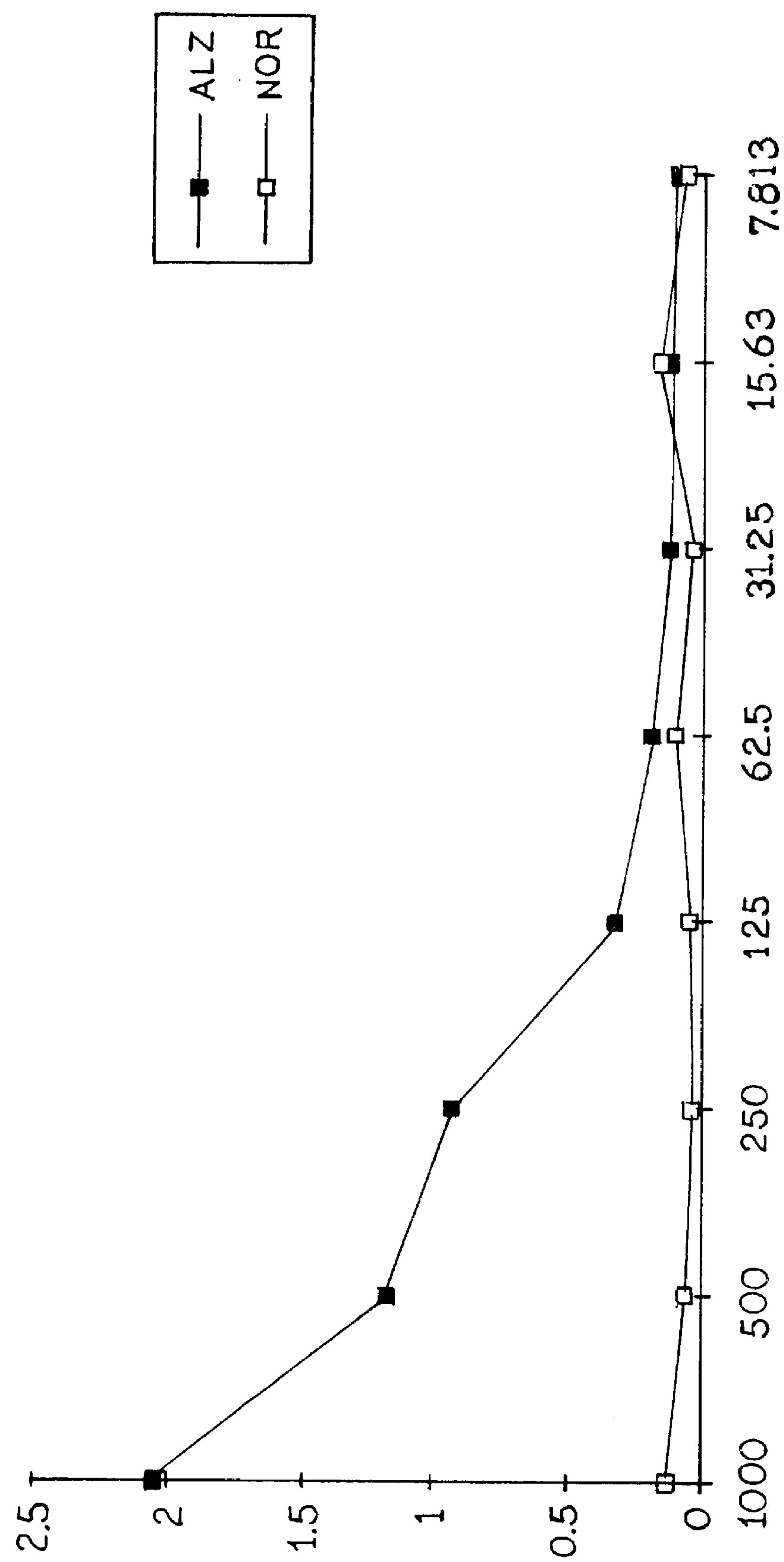
Figure 7M:
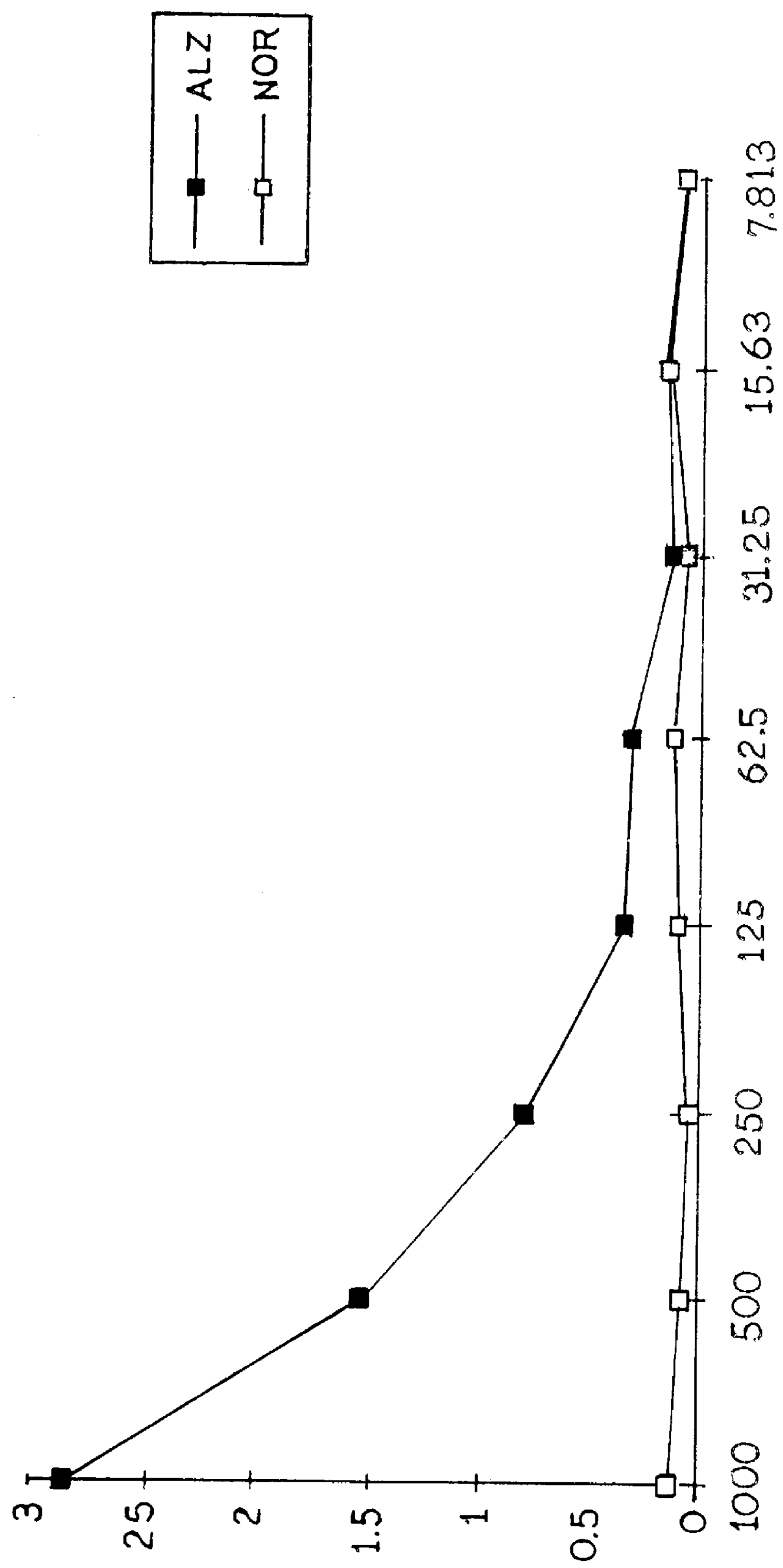

The monoclonal antibodies obtained are: TG3, TG4, TG5, MC1, MC2, MC3, MC5, MC6, MC15, MC16, and PHF-1. FIG. 6 shows reactivity of some of these monoclonal antibodies with 6 different purified Alzheimer's antigen preparations. Some of these antibodies (e.g., antibody MC1) are very similar in specificity to AlZ-50. Other antibodies react with higher affinity and detect fragments of the Alzheimer's antigen (e.g., antibodies MC6, MC15, TG4 and TG5).

The specificity of the antibodies of the invention for the Alzheimer's antigen is as follows. Under certain conditions ALZ-50 reacts with normal and recombinant tau; however, in the same assay configuration under similar conditions, its reactivity against the Alzheimer antigen is much greater. In fact under other modified conditions, such as the ELISA configurations described in this invention, ALZ-50 only reacts with the Alzheimer antigen. Similarly, the TG-3 epitope can be generated on recombinant tau by appropriate phosphorylation; its reactivity against the Alzheimer antigen is also vastly greater than with phospho recombinant tau. Indeed, the reactivity of many of the antibodies of the invention have epitopes on the tau molecule that are conformationally derived. Some recognize epitopes that are discontinuous (ALZ-50, MC1), while others bind to epitopes that are both discontinuous and phosphorylation dependent (TG-3, TG-4). Presumably, they react much better with the Alzheimer antigen because the tau protein in the abnormal protein complex is "locked" into a preferred conformation for antibody recognition and binding. For these reasons, the lower reactivity of the antibodies with "normal brain proteins" is not problematic because a differential in antibody reactivity exists in Alzheimer's Disease due to the formation of the highly reactive Alzheimer antigen.

Epitope Mapping Procedure

The nature of the biding of Alzheimer antibodies to the Alzheimer antigen was determined by epitope mapping. Since tau is known to be a major component of the Alzheimer antigen, many of the Alzheimer antibodies would bind to either recombinant tau or phosphorecombinant tau. Although the affinities for the recombinant protein would undoubtedly be less than the antibody affinity for the Alzheimer antigen, useful information could still be obtained as to the sites of interaction of the antibodies.

Alzheimer antigen epitopes were identified through deletion analysis of htau40, the full-length, 441-residue form of human central nervous system tau. First, a library of 42 internal deletions spanning the entire tau molecule was created through restriction and religation of htau40 cDNA. The mutants were placed into a bacterial expression vector and transformed into *E. coli*. The resultant library of tau deletions was processed like other bacterial expression libraries (Helfman et al., Focus 6: 1–05, 1984), but was "probed" with the monoclonal antibodies described herein. For identification of phosphoepitopes, membrane-bound lysates of bacterial colonies containing individual clones of the expression library were incubated with a crude mixture of protein kinases in a solid-phase phosphorylation assay (Carmel and Kuret, Anal. Biochem. 203: 274–280, 1992). By assessing the ability of each monoclonal antibody to react with each tau deletion mutant, regions of the tau molecule essential or contributory to antibody binding were identified in Table A.

TABLE A

EPITOPE MAPPING OF ALZHEIMER ANTIGEN ANTIBODIES ON NONPHOSPHORYLATED AND PHOSPHORYLATED RECOMBINANT TAU[1]

| Antibody | Epitope | Location[2] | Resolution (residues) |
|---|---|---|---|
| NONPHOSPHOEPITOPES | | | |
| TG5 | continuous | SER$^{210}$-Ser$^{241}$ | 14 |
| MC1 | discontinuous | Essential[3]: Thr$^{319}$-Lys$^{331}$ | 13 |
| ALZ50 | discontinuous | Essential: Ala$^{2}$-Tyr$^{18}$ | 39 |
| | | Weak[3]: Leu$^{243}$-Lys$^{281}$ | |
| | | Essential: ALA$^{2}$-Tyr$^{18}$ | 17 |

TABLE A-continued

EPITOPE MAPPING OF ALZHEIMER ANTIGEN ANTIBODIES ON NONPHOSPHORYLATED AND PHOSPHORYLATED RECOMBINANT TAU[1]

| Antibody | Epitope | Location[2] | Resolution (residues) |
|---|---|---|---|
| PHOSPHOEPITOPES[4] | | | |
| PHF-1 | continuous | $Lys^{395}$-$Thr^{427}$ | 33 |
| MC15 | continuous | $Leu^{284}$-$Val^{318}$ | 35 |
| TG3 | discontinuous | Essential: $Ser^{210}$-$Ser^{241}$ | 32 |
| | | Weak: $Arg^{242}$-$Lys^{281}$ | 40 |
| | | Weak: $Lys^{395}$-$Thr^{427}$ | 33 |
| TG4 | continuous | Essential: $Ser^{210}$-$Ser^{241}$ | 32 |
| | | Weak: $Arg^{242}$-$Lys^{281}$ | 40 |

[1]Numbering of amino acid residue is according to the longest isoform of 4-repeat central nervous system tau.
[2]Actual epitopes fall within the sequences listed.
[3]Essential indicates that no binding can occur if deletion includes these residues, and Weak indicates that binding is diminished if the residues are deleted.
[4]Phosphorylation was performed using a crude kinase preparation isolated from in vitro-assembled microtubules.

The hybridoma secreting monoclonal antibody TG3 was deposited under the Budapest Treaty with the American Type Culture Collection, Rockville, Md. on Oct. 26, 1994, catalogued as ATCC No. HB 11744 and found viable on Nov. 4, 1994. This monoclonal antibody binds to the region on tau shown in Table A below.

The hybridoma secreting monoclonal antibody TG4 was deposited under the Budapest Treaty with the American Type Culture Collection, Rockville, Md. on Oct. 26, 1994, catalogued as ATCC No. HB 11745 and found viable on Nov. 4, 1994. This monoclonal antibody binds to the region on tau shown in Table A.

The hybridoma secreting monoclonal antibody PHF-1 was deposited under the Budapest Treaty with the American Type Culture Collection, Rockville, Md. on Oct. 26, 1994, catalogued as ATCC No. HB 11743 and found viable on Nov. 4, 1994. This monoclonal antibody binds to the region on tau shown in Table A.

The hybridoma secreting monoclonal antibody MC16 was deposited under the Budapest Treaty with the American Type Culture Collection, Rockville, Md. on Oct. 26, 1994, catalogued as ATCC No. HB 11742 and found viable on Nov. 4, 1994.

The hybridoma secreting monoclonal antibody MC6 was deposited under the Budapest Treaty with the American Type Culture Collection, Rockville, Md. on Oct. 26, 1994, catalogued as ATCC No. HB 11740 and found viable on Nov. 4, 1994.

The hybridoma secreting monoclonal antibody MC1 was deposited under the Budapest Treaty with the American Type Culture Collection, Rockville, Md. on Oct. 26, 1994, catalogued as ATCC No. 11736 and found viable on Nov. 4, 1994. This monoclonal antibody binds to the region on tau shown in Table A.

The hybridoma secreting monoclonal antibody TG5 was deposited under the Budapest Treaty with the American Type Culture Collection, Rockville, Md. on Oct. 26, 1994, catalogued as ATCC No. HB 11746 and found viable on Nov. 4, 1994.

The hybridoma secreting monoclonal antibody MC2 was deposited under the Budapest Treaty with the American Type Culture Collection, Rockville, Md. on Oct. 26, 1994, catalogued as ATCC No. HB 11737 and found viable on Nov. 4, 1994. This monoclonal antibody binds to the region on tau shown in Table A.

The hybridoma secreting monoclonal antibody MC3 was deposited under the Budapest Treaty with the American Type Culture Collection, Rockville, Md. on Oct. 26, 1994, catalogued as ATCC No. HB 11738 and found viable on Nov. 4, 1994.

The hybridoma secreting monoclonal antibody MC5 was deposited under the Budapest Treaty with the American Type Culture Collection, Rockville, Md. on Oct. 26, 1994, catalogued as ATCC No. HB 11739 and found viable on Nov. 4, 1994.

The hybridoma secreting monoclonal antibody MC15 was deposited under the Budapest Treaty with the American Type Culture Collection, Rockville, Md. on Oct. 26, 1994, catalogued as ATCC No. HB 11741 and found viable on Nov. 4, 1994. This monoclonal antibody binds to the region on tau shown in Table A.

3. Rabbit anti-ALZ IgG

Alzheimer's disease brain homogenates were enriched for Alzheimer's antigen by multiple differential centrifugation steps and detergent extractions. Rabbits were immunized with highly enriched Alzheimer's antigen fraction and boosted according to a monthly schedule. Bleeds were screened by using ELISA in which the immunogen preparation was dried in the wells by forced air at 37° C. After desired titers were achieved, rabbit sera were purified by protein-A affinity chromatography.

The Protein A purified IgG from the serum bleeds of these rabbits was used to coat beads used in the assays described below.

EXAMPLE 2

Isolation and Characterization of Alzheimer's Disease Antigen

Monoclonal antibodies specific for the Alzheimer's disease antigen were assayed so as to determine their ability to bind to Alzheimer brain homogenate using a known technique referred to in the prior art as enzyme linked immunosorbent assay (ELISA). The brain homogenate was prepared using 2.5 g of Alzheimer cortex homogenized into 10 ml of phosphate buffered saline (PBS) containing 1 mM phenyl methyl sulfonyl fluoride by passes of a glass pestle in a Dounce homogenizer. As used herein, "PBS" refers to a solution of 0.01M sodium phosphate and 0.14M sodium chloride at pH 6.8. The brain homogenate was centrifuged in a BECKMAN JA-21 CENTRIFUGE (Beckman) for twenty minutes at a temperature of about 4° C. at a rate of about 15,000 rpm to produce about 27,200 g. The supernatant of the brain homogenate was removed and loaded onto a chromatographic column containing 350 ml of the molecular sieve SEPHAROSE 6B (Pharmacia). The carrier used for the chromatographic procedure was PBS and was run through the chromatographic column at the rate of 6 ml per hour. Fractions of 3.1 ml were collected.

The Alzheimer's disease antigen largely elutes from the chromatographic column in the void volume. The presence of the antigen in the void volume was identified by use of the enzyme linked immunosorbent assay (ELISA). Fifty microliters of each void volume fraction were tested. Each fifty microliters was diluted with water in a ratio of 1:100 and fifty microliters of this diluted solution was dried onto 96-well polyvinyl microtiter plates (NUNC) for the ELISA. Each dried sample of the antigen was combined with 200 microliters per well of a blocking solution of PBS with 5 percent (v/w) powdered non-fat dry milk, and was incubated in the wells for the ELISA for one hour at room temperature.

The antibody to be tested for the antigen was diluted to a ratio of 1:5 with the blocking solution. Fifty microliters of the diluted antibody solution were added to each well and allowed to incubate for one hour at room temperature. The diluted antibody solution was removed and the polyvinyl microtiter plates were washed five times with an aqueous mixture of 0.01M TRIS (Sigma) and 0.1 percent TWEEN-20 (National Diagnostic) at a pH of 7.4. The dried sample was then incubated for one hour at room temperature with a secondary antibody comprising peroxidase-conjugated goat antibody to mouse immunoglobulins (Kirkegaard & Perry). Thereafter, the secondary antibody was removed and the polyvinyl microtiter plates were washed five times with an aqueous mixture of 0.01M TRIS and 0.1 percent TWEEN-20. The sample was incubated for 30 minutes at room temperature with a solution of 2,2'-azino-di'-3-ethylbenzthiazoline solution (ABTS) (Kirkegaard & Perry). Fifty microliters per well was used. Subsequently, the ELISA reader was used with a 405 nm filter to measure optical density. Color development with the ABTS indicates the presence of antibodies bound to antigens.

Antibody ALZ-50 was found to be specific for the Alzheimer's disease antigen under the assay conditions described. Table 1, below, shows the results of antigen measurements from a pool of temporal cortices of both patients who died of Alzheimer's disease and normal individuals. Ten Alzheimer cases and six normal cases were used for the analysis. The Alzheimer's disease cases were typical in both clinical and neuropathological features. Brain homogenates were prepared from normal individuals dying in hospitals from lung or heart diseases. These patients were not demented prior to death and had no history of neurologic or psychiatric disease. Neuropathologic studies failed to reveal Alzheimer's disease pathology in the normal individuals.

TABLE 1

| Protein Microgram/Well | 0.33 | 1.0 | 3.3 | 10.0 |
|---|---|---|---|---|
| Optical Density x100 Alzheimer | 75 | 215 | 410 | 530 |
| Optical Density x100 normal | 10 | 30 | 50 | 80 |

It can be seen in Table 1 that 0.33 microgram of temporal cortex homogenate from an Alzheimer's disease patient had an optical density of 75, whereas the temporal cortex homogenate from a normal patient had an optical density of only 10. Hence, the Alzheimer's disease antigen is 7 to 8 times greater in concentration in the temporal cortices of Alzheimer patients as compared to normal patients.

An additional study was performed using the cases listed in Table 2. All cases were diagnosed by standard neuropathologic techniques. Cases of individuals who were not neurologically impaired prior to death and exhibited no abnormal neuropathologic changes upon autopsy are described as normal. For immunocytochemistry, the tissue was fixed in formalin until use. The tissue used in the biochemical studies was stored frozen at −80° C. until use. Cerebrospinal fluid was obtained by lumbar puncture from 9 patients undergoing evaluation for dementia. Neurologic examinations included CT scan, EEG, routine blood chemistry and neuropsychologic testing. These individuals were all assigned a diagnosis of primary degenerative dementia, probably due to Alzheimer's disease. Samples were obtained from 5 females and 4 males ranging in age from 60 to 76. Samples from non-demented individuals were obtained from 3 males and 3 females, ranging in age from 60 to 93. Immunochemical reagents used included peroxidase-coupled goat antimouse antibody (Biorad Labs.), Iodine-125-coupled goat antimouse antibody (Amersham Corp.) and the peroxidase substrate 2,2'-Azino-di(3-ethylbenzthiazoline sulfonate (ABTS, Biorad Labs.).

Quantitation of the amount of Alzheimer's disease antigen-antibody immunoreactivity was performed using an enzyme linked immunosorbent assay (ELISA). Brain tissue was homogenized in 10 volumes of PBS pH 6.8 plus 2 mM EDTA, 1 mM phenylmethyl sulfonyl fluoride. The concentration of protein present in the samples was determined by a Biorad protein assay. The homogenate was dried onto polyvinyl plates by adding 100 mg of protein per well and serially diluting the amount of tissue by a factor of three to yield 100 ng of protein per well for the final dilution point. The samples were then incubated with PBS pH 7.4 plus 5% nonfat dry milk (blocking solution) for 1 hour to reduce nonspecific binding and then incubated with Alzheimer antibody hybridoma medium diluted 1:5 in blocking solution for one hour at room temperature. In the procedure described above, the samples of brain homogenates were incubated with Alzheimer antibody overnight in the cold. Antibody was removed by washing the plates five times in 0.01M Tris plus 0.02% Tween-20 and the plates were incubated with peroxidase conjugated goat antimouse antibody diluted 1:500 in blocking solution. Following a final washing as above, presence of antibody was visualized by incubating the samples with ABTS for 30 minutes and reading the optical density at 405 nm.

Immunocytochemistry was performed using vibratome sections (40 microns thick) cut from tissue fixed in formalin. The sections were washed twice in phosphate-buffered saline (PBS), and incubated for 30 minutes in 0.25% Triton X-100-3% hydrogen peroxide. After a PBS wash, the sections were treated as described above for the ELISA assay. The peroxidase was visualized by reaction with 0.45 mg/ml diaminobenzidine and 0.44 mM hydrogen peroxide in 0.1M Tris, pH 7.4.

For Western blot analysis, PBS-2 mM EDTA insoluble material was dissolved in 5% SDS-5% beta-mercaptoethanol and fractionated on 10% SDS-polyacrylamide gels. Proteins were transferred to nitrocellulose, and the Alzheimer antibody staining was performed as described above, except that $^{125}$I-labeled goat anti-mouse immunoglobulin was used as the secondary antibody, and the pattern of reactivity was visualized by autoradiography.

The amount of immunoreactivity present in each sample was first determined using an enzyme linked immunosorbent assay (ELISA). The results are shown in Table 2 below.

was apparent, hippocampal tissue exhibited pyramidal layer neuronal staining, and thioflavin S stains revealed the presence of both neuritic plaques and neurofibrillary tangles. These results suggest that this individual may have suffered from both Parkinson's and Alzheimer's disease and that the plaques were neuritic plaques containing Alzheimer antigen.

Tissue from a case of Down's Syndrome who died at age 52 and had numerous plaques and tangles in the cerebral cortex reacted in a manner similar to Alzheimer disease specimens. This is consistent with the hypothesis that older Down's Syndrome individuals are affected by Alzheimer's disease. No staining was found in tissue affected by any of the other diseases listed in Table 2. Nor was staining found in normal tissue, even when the tissue had small numbers of diffuse amyloid plaques present. The composition of plaques in the Alzheimer brain are distinct from those in the normal aged brain in that they are neuritic in nature containing dystrophic neurites with Alzheimer antigen of the invention.

TABLE 2

OCCURRENCE AND QUANTITATION OF ALZHEIMER ANTIBODY IMMUNOREACTIVITY

| Diagnosis | Immunocytochemical Reactivity in Cortex | n | Quantitation* of Cortical Reactivity | (n) | Relative Reactivity |
|---|---|---|---|---|---|
| A. | | | | | |
| Alzheimer's | ++++++ | (40) | 1.42 ± 0.73 | (8) | 100.0 |
| Pick's | ++ | (3) | 46.40 ± 9.20 | (3) | 3.1 |
| GPD | + | (2) | 48.00 ± 8.00 | (2) | 3.0 |
| Parkinson's with cortical plaques | – | (2) | 16.9, 100 | (2) | 2.4 |
| Parkinson's with Alzheimer's | ++ | (1) | ND | | |
| Normal | – | (18) | 79 ± 27 | (7) | 1.8 |
| B. | | | | | |
| Down's Syndrome | +++++ | (1) | | | |
| Hallervorden-Spatz | + | (1) | | | |
| Huntington's | – | (1) | | | |
| Diffuse Lewy Body | – | (3) | | | |
| Unclassified Dementia | – | (3) | | | |

ND = not determined

*μg of protein required to produce an O.D. of 0.5 in the ELISA.

The amount of immunoreactivity present in Alzheimer's tissue was far greater than that found in tissue affected by Guam Parkinson Disease (GPD), Pick's Disease, Parkinson's Disease with cortical plaque pathology (PD) or normal tissue. When normalized, the amount of immunoreactivity in each disease is, respectively, 100, 3.0, 3.1, 2.4 and 1.8.

The immunocytochemistry of the Alzheimer antibody was examined in cases representing the diseases described in Table 2, sections A & B. One of the dramatic characteristics of Alzheimer antibody staining is the extensive staining of abnormal neurites. When observed grossly, the neuritic staining accounts for most of the visible staining. Staining of neurons was found in GPD and Hallervorden-Spatz Disease (HSD) and staining of Pick bodies was found in Pick's disease. In contrast to the extensive neuritic staining present in tissue from cases affected by Alzheimer's disease, tissues affected by GPD, HSD or Pick's Disease exhibit minimal neuritic staining. PD cortical tissue, though pathologically similar to Alzheimer's tissue, exhibited only a small amount of staining of plaques in one case and no staining in the other two cases. In the one PD case in which staining of plaques The number of tangles seen in Alzheimer's disease tissue was less than the number of Pick bodies present in the inferior temporal cortex of the cases of Pick's Disease, and more than triple that present in GPD or HSD tissue. The amount of immunoreactivity present did not differ in affected neurons of different diseases or in Pick bodies. Hence, the difference in levels of immunoreactivity is due to abundant staining of abnormnal neurites present in Alzheimer tissue. Thus, the total amount of immunocytochemical staining correlated with the total amount of immunoreactivity seen by ELISA.

The small amount of immunoreactivity in other disease tissues such as those from Pick's Disease and GPD corresponds to the low level presence of the Alzheimer's disease antigen. This was determined using Western blot analysis with the Alzheimer antibody. In order to maximize the amount of Alzheimer protein present in the samples used, the samples were prepared in the presence of 2 mM EDTA, which decreases the solubility of the Alzheimer protein up to 90%. This decreased solubility was discovered when an attempt was made at stabilizing Alzheimer antigen by the addition of a cocktail of protease inhibitors, including EDTA. Alzheimer antibody reactivity was virtually absent from supernatant fractions prepared in the presence of EDTA, but was quantitatively recovered in the pellets. The addition of 2 mM EDTA to homogenates thus provides a convenient enrichment of antigen.

The PBS-2 mM EDTA insoluble fractions were examined by Western blot analysis with Alzheimer antibody. In order to maximize the sensitivity of the blot for all types of binding, large amounts of protein were loaded on the gel, and incubated overnight with Alzheimer antibody, and I-125 labeled secondary antibody. The immunoreactivity in Alzheimer's disease tissue corresponded to a 68,000–62,000 dalton protein doublet. In addition, faint higher molecular weight bands were also seen above the doublet. Normal tissue contained a great deal of lower molecular weight immunoreactivity. This results from the use of large amounts of crude material. These bands did not appear when partially purified samples are examined and no Alzheimer's disease antigen was detected in purified fractions from normal or other neurologic diseases. The lower molecular weight cross-reactive proteins account for the normal brain tissue immunoreactivity measured by ELISA with overnight incubations.

There was no reactivity in the 68,000 dalton region of the immunoblot in preparations from normal tissues. Tissue from Pick's Disease cases contained mostly 62,000 dalton protein and lower molecular weight material. A faint band in the 68,000 dalton region was also seen. GPD tissue gave a sharp immunoreactive band at 62,000 daltons and diffuse reactivity in the 68,000 dalton region. These results suggest that the trace levels of immunoreactivity seen by immunocytochemistry in Pick's Disease and GPD represents the same protein as that seen in the Alzheimer brains, that is the Alzheimer protein complex (Alzheimer antigen) containing the 68,000 dalton polypeptide. The degree of elevation of this protein in the Alzheimer brain is clearly evident in spite of the use of half as much tissue in the Alzheimer lane in order to prevent Alzheimer reactivity from obscuring reactivity in neighboring lanes.

The selective elevation of the abundance of the Alzheimer antigen in Alzheimer tissue can be exploited in diagnostic testing for Alzheimer's disease. The usefulness of this antigen is shown below in the following examples.

The Alzheimer's disease antigen of the invention is recognized by Alzheimer's disease-specific antibodies, and is present in high quantities in Alzheimer's disease patients and present in vanishingly small amounts in non-Alzheimer's disease patients, including patients suffering from other neurologic diseases. The Alzheimer's disease antigen is at least about 50 percent soluble in PBS and largely elutes from a molecular sieve column such as SEPHACRYL S-400 or SEPHADEX G-25 or SEPHAROSE 6B at the void volume which corresponds to a molecular weight of at least $2\times10^6$ daltons. This indicates that the Alzheimer's disease antigen is an aggregate of several proteins. The inventors have discovered that some of the proteins that make up the Alzheimer's disease antigen have molecular weights of about 53,000, 62,000, 68,000, and 105,000 daltons. Further, the Alzheimer's disease antigen contains tau and phosphorylated tau, binds tightly to Affi-blue columns and does not elute off with aqueous 0.5M sodium chloride but can be removed with aqueous 2M sodium chloride.

The molecular weight of the major protein comprising the Alzheimer's disease antigen is about 68,000 daltons after denaturation with sodium dodecyl sulfate (SDS) and reduction with mercaptoethanol. The apparent molecular weight of the Alzheimer's antigen in nonreduced form after denaturation with SDS is much greater than 68,000 daltons, being greater than about 300,000 daltons. In nonreduced form, the Alzheimer's disease antigen will not enter a 10 percent acrylamide gel.

The pI of the Alzheimer's disease antigen in reduced or nonreduced form is about 6 as determined by isoelectric focusing. The antigen precipitates in 50 percent saturated aqueous ammonium sulfate at 4° C., and co-purifies with and is thought to be a kinase which will phosphorylate molecules in the presence of magnesium ($Mg^{++}$) and adenosine triphosphate (ATP). The Alzheimer's disease antigen does not co-purify with neurofilaments.

The following summarizes some of the properties of an Alzheimer antigen:

1. An Alzheimer antigen is recognized by Alzheimer antibody.

2. An Alzheimer antigen is present in Alzheimer patients and substantially absent from non-Alzheimer patients, including patients suffering from other neurologic diseases.

3. An Alzheimer antigen is at least about 50 percent soluble in PBS.

4. An Alzheimer antigen largely elutes from a molecular sieve column such as SEPHACRYL S-400 or SEPHADEX G-25 or SEPHAROSE 6B at the void volume which corresponds to a molecular weight of at least $2\times10^6$ daltons. This suggests that the size of the Alzheimer antigen may represent an aggregated form of the native protein.

5. An Alzheimer antigen binds tightly to Affi-blue columns and does not elute off with aqueous 0.5M sodium chloride but can be removed with aqueous 2M sodium chloride.

6. The apparent molecular weight of one Alzheimer antigen subunit recognized by the Alzheimer antibody is about 68,000 daltons after denaturation with sodium dodecyl sulfate (SDS) and reduction with mercaptoethanol.

7. The apparent molecular weight of the Alzheimer antigen recognized by the Alzheimer antibody in nonreduced form after denaturation with SDS is much greater than 68,000 daltons, being greater than about 300,000 daltons. In nonreduced form, the Alzheimer antigen subunit will not enter a 10 percent acrylamide gel.

8. An Alzheimer antigen precipitates in 50 percent saturated aqueous ammonium sulfate at 4° C.

9. The Alzheimer antigen co-purifies with a protein kinase which will phosphorylate molecules in the presence of magnesium ($Mg^{++}$) and adenosine triphosphate (ATP).

10. An Alzheimer antigen does not copurify with neurofilaments.

11. An Alzheimer antibody reacts with antigen present in the cerebrospinal fluid of Alzheimer patients and absent from the cerebrospinal fluid of normal patients.

12. An Alzheimer antibody reacts with antigen present in Alzheimer's patients and largely absent from patients with Huntington's Chorea, Diffuse Lewy Body Disease, Creutzfeldt Jakob Disease, Progressive Supernuclear Palsy and Multi-Infarct Disease.

13. Trace amounts of Alzheimer antigen may be detectable in cases of Guam-Parkinson Dementia Complex and Pick's Disease. However, accumulation of Alzheimer antigen in neuronal processes appears to be a unique feature of Alzheimer's disease.

14. An aqueous PBS and 2 mM ethylene diamine tetraacetic acid solution has a solubility of about 10% for Alzheimer antigen. In addition, an aqueous 2 mM ethylene diamine tetra acetic acid solution prevents Alzheimer antigen from being extracted from brain tissue.

Additional measurements show that the Alzheimer antigen was similarly elevated in the nucleus basalis and hippocampus of Alzheimer patients. The cortex, nucleus basalis and hippocampus are known to contain neuritic plaques, abnormal neurites, and neurofibrillary tangles in brains of patients with Alzheimer's disease. Tests made on brain areas known to be less affected by the disease, such as caudate, thalamus, and cerebellum demonstrated little or no reactivity. Thus, the procedure described herein enables the identification of an antigen (Alzheimer antigen) closely associated with Alzheimer's disease and antibodies (Alzheimer antibodies) which identifies the antigen.

EXAMPLE 2A

Isolation of Alzheimer Antigen: Alternative Procedure

The concentration of Alzheimer antigen in a sample from an Alzheimer patient can be increased by at least $10^3$ times and preferably at least $10^5$ times to simplify the study and detection of the Alzheimer antigen. A concentrate of the Alzheimer protein is obtained using the following procedure: A portion of an Alzheimer brain is homogenized at 4° C. for 30 seconds in 4 volumes of a buffer comprising PBS and 1 mM phenyl methyl sulfonyl fluoride, having a pH of 6.8. This amounts to a ratio of 1 gram of brain per 4 ml. The homogenization is carried out in a teflon-glass homogenizer with a minimum of three strokes of a piston turning at 2,000 rpm. The brain homogenate is centrifuged for 23 minutes at 4° C. at 27,200 g. After the centrifuging, the supernatant is loaded into a chromatographic column containing SEPHACRYL-S-400 (Pharmacia) and eluted with the PBS. The Alzheimer antigen appears in the void volume from the chromotagraphic column and is monitored using the ELISA. Subsequently, the void volume is run over an Affi-blue column (Bio-Rad). The Affi-blue column is washed with 20 column volumes of the PBS. The Alzheimer protein remains bound to the Affi-blue column. The Alzheimer protein is eluted off of the Affi-blue column with 2M aqueous sodium chloride. That is, the concentration of sodium chloride in the buffer increases during the elution from 0.5M to 2M.

The presence of the Alzheimer antigen can be monitored using the ELISA. The sodium chloride is removed from the Alzheimer antigen by using a chromatographic column comprising SEPHADEX G-25 (Pharmacia) and eluting with buffer PBS. The Alzheimer protein elutes largely in the void volume. The void volume containing the Alzheimer protein is loaded onto an Alzheimer antibody immunoaffinity column and the column is washed with at least 20 column volumes of the PBS. The Alzheimer antigen is eluted with aqueous 3M KSCN. The elution is monitored for the presence of the Alzheimer protein. The eluted solution with the Alzheimer protein is desalted using the SEPHADEX G-25 column with PBS. Instead of PBS, a buffer solution containing 0.001M sodium phosphate and 0.014M sodium chloride at pH 6.8 can be used to provide a more concentrated elution of Alzheimer antigen. Further concentration of the Alzheimer antigen, as much as 10 fold, can be accomplished by removal of water from the eluted sample by heating under vacuum. The resulting concentration is about 1 percent by weight.

Samples of the concentrated Alzheimer and normal cortex were studied using Western blot technique, i.e., as disclosed in *Gene Analysis Techniques*, by D. A. Johnson and J. W. Yauster, Vol. 1., pp. 3–8 (1984). A major electrophoretic species contained as part of the Alzheimer antigen was found to have an apparent molecular weight of about 68,000 daltons. The reactivity of the normal brain void volume fraction from a SEPHAROSE 6B (Pharmacia) column was detected on the Western blot by loading onto the polyacrylamide gel three times as much normal protein as was used for the Western blot of the Alzheimer void volume fraction. The major band for the normal brain void volume had a molecular weight of 59,000 daltons and a doublet at 245,000 daltons. When reduced, the Alzheimer antigen has a molecular weight of about 62,000 to about 68,000 daltons, and is distinctively different from the antigen having a molecular weight of 59,000 daltons from brain showing no signs of Alzheimer's disease. These results show that in 0.01M tris-buffered saline (TBS) the Alzheimer antigen is aggregated, or part of a larger complex.

Several proteins having subunits with molecular weights of about 68,000 daltons are distinguishable from the Alzheimer antigen. These proteins are in two families: in the cytoskeletal family there are neurofilaments and normal tau proteins, and in the cholinergic family there is choline acetyltransferase. None of these proteins exhibit an elevated concentration in Alzheimer brains as compared to normal brains. If the Alzheimer protein is related to the protein having a molecular weight of about 59,000 daltons and found in normal brains, then the Alzheimer antigen is unlikely to be neurofilament, normal tau protein, or choline acetyltransferase.

Additional studies were performed to compare samples of brain tissues for several different subjects: two cases of Guam Parkinson's disease, two cases of Pick's disease, six cases of Alzheimer's disease, two cases of Alzheimer's disease combined with Parkinson's disease and ten neurologically normal subjects. All of the cases were diagnosed by neuropathology. Studies were made of the immunoreactivity and immunochemistry of the samples of brain tissues. Initially, the amount of immunoreactivity in each sample was found using ELISA on crude brain homogenates. For each sample of brain tissue, a crude brain homogenate was prepared by fractionating brain tissue into soluble and insoluble portions using PBS and 2 mM ethylene diamine tetra acetic acid and centrifuging at about 27,000 g for about 25 minutes. The supernatant was removed and the pellet was homogenized in PBS. The concentration of protein present in each pellet was determined using the Bio-Rad protein assay.

Dilution curves were carried out on each sample and the amount of immunoreactivity in each sample was determined using the ELISA to determine the presence of the reaction of each sample with Alzheimer antibody. The results of these measurements on the crude brain homogenates showed that significant amounts of immunoreactivity are found only in Alzheimer disease cases. Comparison of the amounts of immunoreactivity shows that the immunoreactivity is significantly elevated over that measured in other neurologic diseases.

For immunocytochemical studies, brain tissue samples were fixed in formalin until the tests were carried out. The immunocytochemistry study was performed using the Alzheimer antibody on brain tissue from Guam Parkinson's disease, Picks disease, Alzheimer's disease, Alzheimer's/Parkinson's disease and normal subjects. The Alzheimer antibody stained neurons, neuritic plaques and abnormal neurites in the Alzheimer brain sample. One of the characteristics of the Alzheimer antibody is that the staining is dramatic and extensive for the abnormal neurites. When observed closely, the neuritic staining accounts for most of the visible staining. Staining of some neurons is found in Guam Parkinson's brain tissue and staining of the Pick bodies is found in Pick's brain tissue. The Guam Parkinson's brain tissue exhibits no neuritic staining and Pick's brain tissue exhibits little neuritic staining. The Alzheimer's-Parkinson's cortical tissue is pathologically similar to Alzheimer's brain tissue but exhibited only a small amount of stained neuritic plaques in one case and no staining in two other cases. Hippocampal tissue from one case exhibited pyramidal layer neuronal staining but there was little neuritic staining. No staining is observed for normal brain tissue even when a small number of neuritic plaques are present. The total amount of immunocytochemical staining correlates well with the total amount of immunoreactivity observed by the ELISA. The primary difference in the levels of immunoreactivity was due to the neuritic (abnormal neurite) staining for Alzheimer's brain tissue.

EXAMPLE 3

Antibody Staining of Normal and Alzheimer's Brain Tissue

The Alzheimer's disease-specific antibodies of the invention react with Alzheimer's antigen which is present in the cerebrospinal fluid of Alzheimer's disease patients and absent from the cerebrospinal fluid of normal patients and patients with Huntington's Chorea, Diffuse Lewy Body Disease, Cruetzfeldt Jakob Disease, Progressive Supranuclear Palsy and Multi-Infarct Disease.

Immunocytochemistry of the Alzheimer ALZ-50 antibody on formalin-fixed brain tissue showed that the antibody was highly selective for abnormal neuritic components in the Alzheimer brain. Many neurons in the pyramidal layer of the hippocampus were stained. The Alzheimer antigen was found to be present in cell bodies and in abnormal neurites. In addition, neuritic plaques were strongly stained by the Alzheimer antibody. The staining was confined to the neuritic meshwork present in plaques. Strongly stained neurons and neuritic plaques were found throughout Alzheimer hippocampus and cortex. In contrast, there was virtually no staining of normal brain. This pattern of specificity was observed in 40 brains from Alzheimer patients and 16 brains from normal subjects.

EXAMPLE 4

Antibody Staining of Neurons and Neurofibrillary Tangles

The relationship between the antibody staining of neurons and the presence of neurofibrillary tangles was determined using a double staining technique. Vibratome sections of formalin-fixed Alzheimer tissue react with the Alzheimer antibody and the immunoreactivity was visualized with the use of the peroxidase conjugated goat antibody to mouse immunoglobulins. The peroxidase reaction was made visible by the use of 4-chloronaphthol. 4-Chloronaphthol is a peroxidase substrate and reacts to produce a product that precipitates in an aqueous solution but is soluble in organic solvents. The tissue section was photographed and the 4-chloronaphthol was removed by dehydration and xylene treatment. Thereafter, plaques and tangles were stained with thioflavin S, a known sensitive histologic reagent for the demonstration of these lesions, and the section was photographed again. Study of the photographs and the staining patterns indicated that many neurons are stained both by the Alzheimer antibody and by thioflavin S. Some neurons are darkly stained by the Alzheimer antibody and do not appear to contain neurofibrillary tangles. A small fraction of neurons contain tangles and are thioflavin-positive but are not positive for the Alzheimer's disease antigen. The staining of plaques by Alzheimer antibody was also studied by this method. The Alzheimer antibody revealed more plaques than did the thioflavin. The plaques positive for Alzheimer antibody contained dystrophic neurites and hence were neuritic plaques.

EXAMPLE 5

Antibody Staining of Alzheimer's Antigen and Paired Helical Filaments

The distinction between the Alzheimer antigen and insoluble paired helical filaments (PHF) was determined by biochemical experiments. It was found that Alzheimer antigen is highly soluble in 0.01M tris-buffered saline (hereinafter, TBS) and completely soluble in TBS containing 5 percent by weight sodium dodecyl sulfate (hereinafter, TBS-SDS), in contrast to insoluble paired helical filaments which will not dissolve in either TBS or TBS-SDS. Solubility was tested by vortexing Alzheimer cortex homogenate for two minutes in TBS or TBS-SDS. The brain homogenate was then centrifuged for 10 minutes at 10,000 g. The supernatant and pellet from the centrifugation were separated and the pellet was washed twice by homogenizing and centrifuging as in the first instance. The supernatant and pellet were homogenized in water and various amounts of each sample were dried onto the polyvinyl plates for the ELISA. The amounts were 10, 3 and 1 microgram per 50 microliters. The presence of the Alzheimer antigen was determined using the ELISA. The reactivity of the insoluble paired helical filaments was monitored using a known antibody to paired helical filaments. The Alzheimer antibody showed reactivity in the TBS supernatant and the reactivity was quantitatively recovered in the TBS-SDS supernatant whereas the paired helical filaments reactivity remained in the pellet after the TBS-SDS extraction. Therefore, it can be concluded that the Alzheimer antibody immunoreactivity is soluble and segregates away from insoluble paired helical filament immunoreactivity.

Additional tests were carried out to establish a difference between the Alzheimer antigen and insoluble paired helical filaments. Enzyme experiments confirmed the distinction between the Alzheimer antigen and the paired helical filaments. Portions of the Alzheimer brain homogenates were treated for 0, 20 or 60 minutes with trypsin and portions were similarly treated with alkaline phosphatase prior to being dried onto polyvinyl plates for ELISA. ELISA was used to measure the sensitivity of the Alzheimer antigen epitopes to the treatment. The Alzheimer antigen epitopes are highly sensitive to trypsin in contrast to the insoluble paired helical filaments. This demonstrates that the Alzheimer protein is distinct from insoluble paired helical filaments.

It has recently been shown that the Alzheimer antigen, when viewed in the electron microscope, consists of soluble paired helical filaments (Vincent and Davies, Proc. Natl. Acad. Sci. 89: 2878–2882, 1992). Although also consisting, at least in part, of Alzheimer antigen, the insoluble PHF will not readily dissolve under the solution conditions described above. Alzheimer antigen will dissolve under these solvent conditions.

Although the Alzheimer antigen epitope is not phosphatase sensitive, this does not establish that the Alzheimer antigen is not phosphorylated. It is known that many antibodies to neurofilament epitopes that identify neurofibrillary tangles fail to react after phosphatase treatment. In addition, this suggests that phosphorylation of the Alzheimer antigen epitope does not account for the ability of the Alzheimer antibody to distinguish between the Alzheimer antigen and normal brain antigens.

EXAMPLE 6

Brain Tissue Extract Assays Utilizing Monoclonal and Polyclonal Antibodies

Materials:

ALZ-50, Rabbit anti-ALZ-50, casein, Quantum, Qwik-Wash System, Reaction Plates, Reaction Tubes, OPD Reagent, Gentamicin Sulfate, Nipasept, $H_2SO_4$ Reagent, ¼ inch beads and TDx microcentrifuge were obtained from Abbott Laboratories; HRPO Goat anti IgM conjugate were obtained from Fisher Scientific; microfuge tubes with matching pestle and pestle driver were obtained from Kontes; Protein A was obtained from BioRad; and BSA, Tween 20 and EGTA were obtained from Sigma.

Tissue Preparation:

Frozen brain specimens were thawed at room temperature until they had a firm consistency to prevent splintering during cutting. About 50 to 150 mg of cortical tissue was placed into a microfuge tube. Frontal and temporal brain cortical tissue consistently has higher Alzheimer's antigen levels. Cold homogenization buffer (0.1 mM Tris, 150 mM NaCl containing EGTA Gentamicin sulfate and Nipasept as preservatives) then was added at 4 mL per mg of tissue. The tissue was homogenized in the microfuge tube for about one minute using the matching pestle driven by hand or mechanical motor. The particulate matter was removed from the homogenate by centrifuging it for one minute in a TDx centrifuge or the equivalent. The tissue was processed at 4° C. throughout the preparation. (−70° C. is recommended for longer storage of the homogenate).

More specifically, the following reagents were used in the preparation of Alzheimer disease brain homogenates enriched for Alzheimer's antigen:

[10×] Homogenate Buffer Stock 100 mM Tris 1.5M NaCl 10 mM EGTA pH 6.8

TBS—Tris Buffered Saline 0.01M Tris 0.9% NaCl pH 7.5

100 mM PMSF/ ethanol (Protease inhibitor)

1% of total volume of brain homogenate mixture

The brain regions to be processed were identified and isolated. The tissue was stored at −80° C. and placed at −20° C. overnight. When ready, the tissue was slightly thawed at room temperature in a biohazard hood to aid in dissection. However, the tissue was kept on ice at all times. The dissected tissue sample then was accurately weighed and placed in a polyethylene container surrounded by ice. Four (4) volumes (ml/g) of cold homogenate buffer [1×] were added to tissue sample. PMSF was added to a total volume at a 1:100 dilution, 1 mM final concentration. Prior to use, the Polytron homogenizer was cleansed with several alternating washes of distilled water, followed by ethanol and a final water rinse. The tissue and buffer were homogenized using a Polytron with 15–20 second blasts with equal intervals, at a setting of 5–6 on the instrument dial. (Adequate homogenization of larger samples may require longer blasts or a higher dial setting.) The sample vessel was surrounded by ice and kept as cool as possible during the homogenization process.

After complete homogenization of the tissue, 1 ml of the sample was aliquoted and saved for assay. The remainder was centrifuged at 20K×g for 20 to 25 minutes at 4° C. The resultant low speed supernatant was aspirated and the volume measured. It then was transferred to high speed centrifuge tubes. 1 ml of low speed supernatant was aliquoted and saved for assay (the low speed pellet contains considerable antibody reactivity and may be reextracted by resuspending to the original volume with cold TBS, and centrifuging as above). The high speed centrifuge tube was spun with volumes recorded, at 100K×g, 1 hour at 4° C. The high speed supernatant then was aspirated and 1 ml was aliquoted and saved for assay. The high speed pellet was carefully resuspended in cold TBS at a chosen concentration. Typically, (30×) stock solution was used for Alzheimer brain cortex tissue extract. Small volumes of this concentrated high speed pellet were aliquoted and stored at −80° C.

Samples from each step of the brain preparation were assayed for antibody reactivity and protein concentration.

Bead coating:

Protein-A purified IgG from the serum bleeds of the rabbits was used to coat beads. Standard ¼ inch polystyrene beads were coated by incubating them with rabbit anti-ALZ IgG in Tris Buffered Saline (pH 8.0) for 2 hours at room temperature and blocked with 4% BSA in phosphate buffered saline. Beads then were washed, overcoated with gelatin/sucrose, dried, and stored at room temperature.

The assay of the present invention detects and measures Alzheimer's antigen. The Alzheimer's antigen effectively is captured by the polyclonal IgG coated on the beads. ALZ-50, used as the detection antibody, is allowed to specifically bind to the immobilized antigen and the bound ALZ-50 is subsequently quantified by using an enzyme conjugated anti-mouse IgM (e.g., a horseradish peroxidase linked goat anti IgM and an appropriate substrate).

Experiment 1

Figure 2:
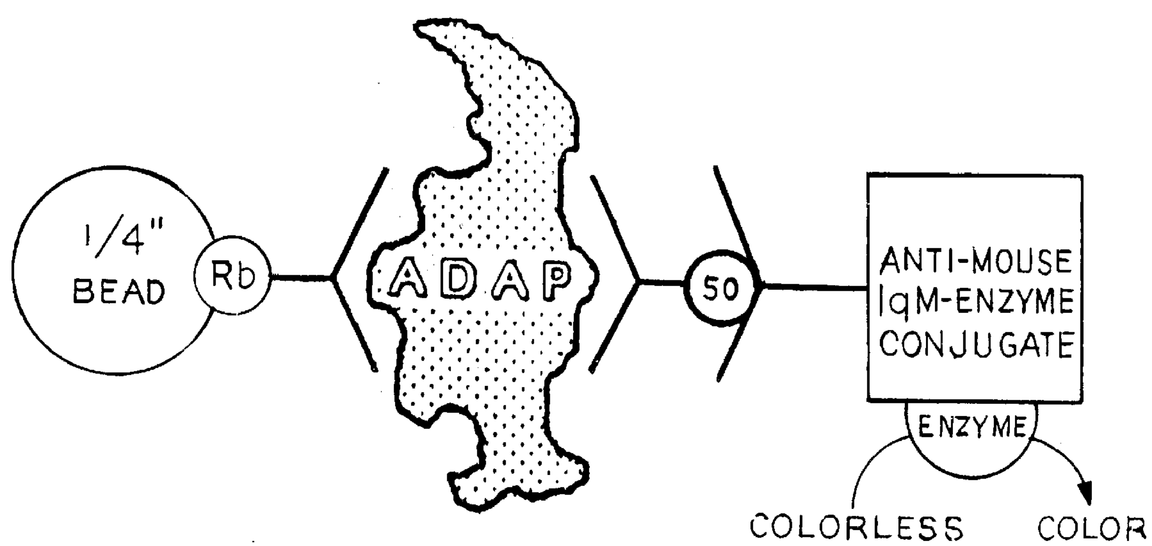
FIG. 2 represents a sandwich immunoassay configuration of the present invention for the diagnosing Alzheimer's disease.

FIG. 2 depicts the configuration of the assay. Post-mortem samples (tissue brain homogenates free of particulate matters) were diluted with sample buffer (1% BSA in PBS, pH 7.5, containing Gentamicin and Nipasept), usually 50 mL of the sample homogenate and 150 mL of the sample buffer. Each sample was run in duplicate. A known negative control and a reagent blank (homogenization buffer instead of sample) were included on each plate. After adding one bead to each well, the plate was covered and incubated for 30 minutes at 37° C. by floating it in a water bath. The beads were washed with distilled water twice using the QwikWash System, and then incubated with 200 mL of an ALZ-50 solution containing about 0.35 mg/ml of IgM (in PBS pH 7.5 containing 0.1% casein, 0.5% Tween 20, Gentamicin and Nipasept) for 30 minutes at 37° C. The beads were washed again (twice), incubated with 200 mL of the HRPO conjugated goat anti mouse IgM diluted in the ALZ-50 diluent buffer containing 1% goat serum and incubated again for 30 minutes at 37° C. The beads were washed twice and transferred to the reaction test tubes according to instructions on the packaging. To each tube containing bead, 300 $\mu$L of OPD solution (prepare as per instructions) were added and incubated at room temperature for 30 minutes. The reaction was stopped by adding 1 mL of 1N sulfuric acid to each tube and the solution was mixed by vortexing. The absorbance of each tube was determined using a Quantum spectrophotometer set to mode O and blanked with distilled water.

This assay procedure was used for detecting the Alzheimer's antigen in samples. However, if measurement of Alzheimer's antigen is desired for comparison of activity among several samples, the samples producing a background corrected absorbance of 0.5 or higher may be diluted serially and the dilution providing the highest absorbance under 0.5 may be used, making sure that the appropriate corrections are made for the dilutions. Moreover, although this assay normalizes the absorbance values to wet tissue weight, the data per unit protein can be expressed for Alzheimer antigen measurement.

Figure 3:
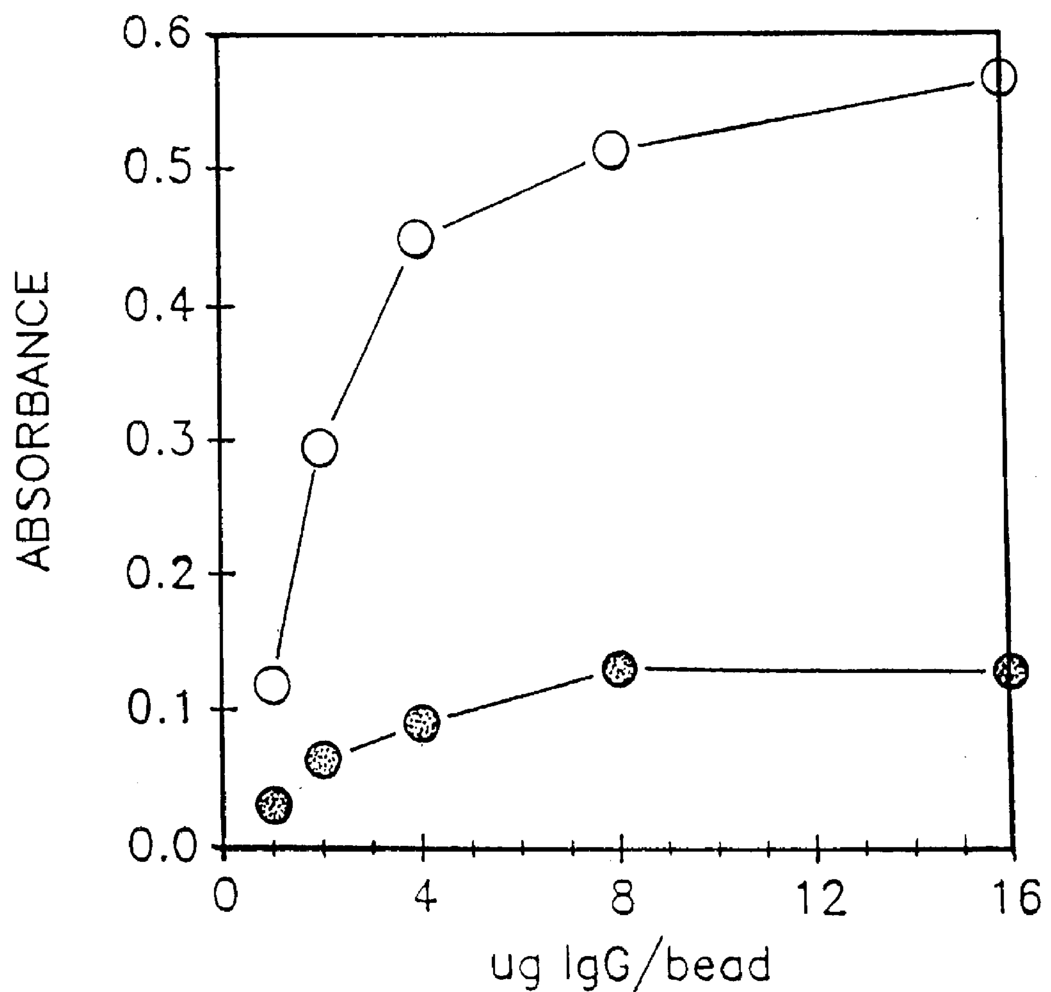
FIG. 3 represents the relationship between absorbance and micrograms IgG/ bead.

With respect to assay optimization, since room temperature was routinely used in manufacturing, only anti-ALZ rabbit IgG amount per bead, time, and pH were optimized. As can be seen in FIG. 3, the background rapidly increased at levels over 2 mg/bead. However, at 4 mg/bead the background was acceptable and the signal approached maximum. Adding 1% goat serum to the conjugate solution considerably lowered the background. No further increase was observed beyond 2 hours and optimum pH was found to be 8.0. The blocking step involved a 30 minute incubation of antibody-coated beads in 4% BSA in PBS. Detection antibody and conjugate concentration were optimized by a standard checker board type titration. Incubation temperatures and durations were chosen to obtain acceptable signal reproducibility in the shortest possible time frame.

Figure 4:
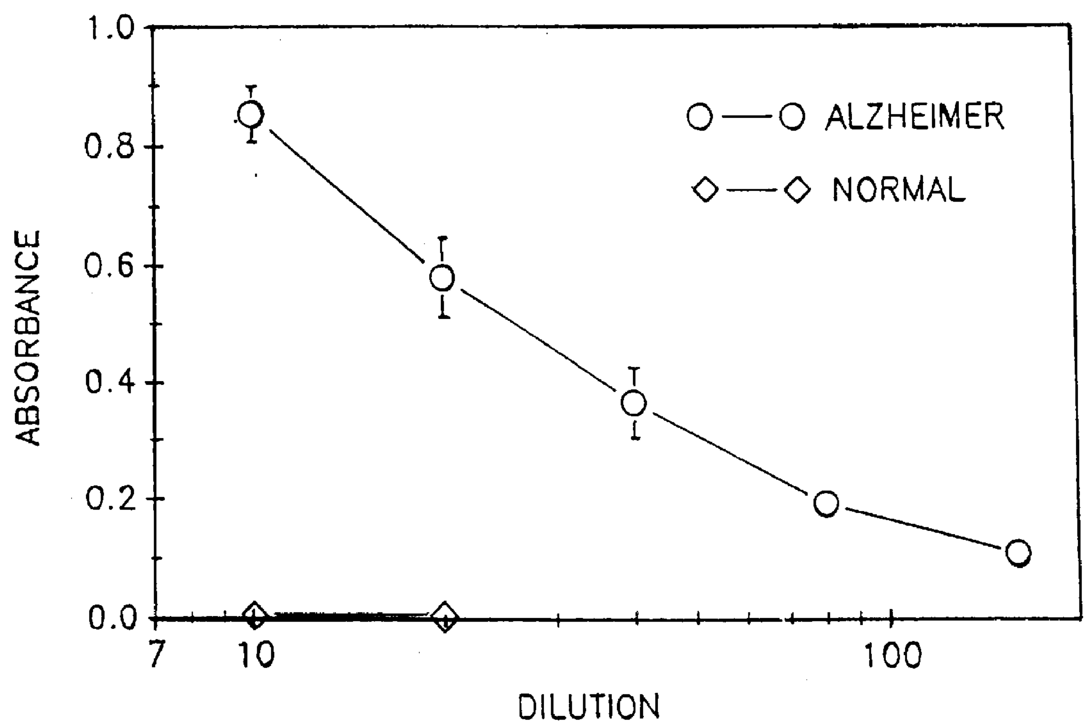
FIG. 4 represents titration curves for Alzheimer's disease brain homogenates and normal brain homogenates.

As to specificity and linearity, FIG. 4 shows that there is no significant reactivity in the normal brain homogenate whereas ALZ-EIA activity in Alzheimer's disease dementia ("AD") brain homogenate titers down. The linear range of the curve is from 0.05 to 0.50.

Table 3 below summarizes the assay's precision. It should be noted that signal for normals and background are essentially identical.

TABLE 3

PRECISION STUDY

| SAMPLE | N | MEAN | SD | MEAN OF WITHIN PLATE CV's |
|---|---|---|---|---|
| AD 1 | 30 | 0.384 | 0.040 | 9.3% |
| AD 2 | 40 | 0.458 | 0.064 | 9.8% |
| NORMAL 1 | 40 | 0.064 | 0.005 | 4.2% |
| NORMAL 2 | 40 | 0.058 | 0.004 | 4.2% |
| BACKGROUND | 40 | 0.056 | 0.007 | 8.5% |

AD 1 is a pool of AD brain homogenates. AD 2 is a homogenate from one AD brain specimen. Similarly, Normal 1 is a pool of non-AD brain homogenates and Normal 2 is a homogenate from one non-AD brain. Background represents assay runs in which homogenization buffer was used instead of brain homogenate. The mean is expressed as absorbance units. The data was accumulated over a period of 2 days. A total of 5 replicates were run per plate and mean of within plate CV's are reported.

Experiment 2

The concentration of an Alzheimer Antigen was measured in post-mortem brain tissue samples of temporal or frontal cortex from 111 human brains. Each of the patients from which the tissue was taken was evaluated clinically (e.g. diagnosis, age, gender and post mortem delay) and all the specimens used were evaluated pathologically prior to the biochemical analyses. There were 27 normal controls (NC), 28 neurological disease controls (NDC), and 53 Alzheimer's disease (AD) of which seven were designated as Senile Dementia of Alzheimer's Type (SDAT), and three older Down's Syndrome with Alzheimer's neuropathology D/AD. The cases in the neurological disease control category included: Parkinson's Disease (n=16), Multi-infarct Dementia (n=5), Huntington's Disease (n=2), Amyotrophic Lateral Sclerosis (n=2), Wernicke's Encephalopathy (n=1), and Korsakoff's syndrome (n=2). The AD group included the following categories: AD, SDAT and D/AD (Down's with AD neuropathology) and the non-AD group included the following categories: NC (normal control) and NDC.

The tissue sample, which ranged in wet weight from 20 to 200 mg, was mixed with 4 volumes of homogenization buffer (0.05M TRIS HC1 at pH=6.8, 1 mM EGTA and 150 mM NaCl) and then homogenized gently with a Kontes motorized pestle inside a standard 1.5 ml conical capped tube. The homogenate was centrifuged at 9500×g for 5 minutes. A duplicate of 50 mL aliquot of the supernatant (equivalent to 10 mg wet tissue) was used in the assay. In each case, Alzheimer antigen results were expressed as absorbance per mg of protein or as absorbance per 10 mg wet tissue weight. All absorbance readings for samples were corrected to net absorbance by subtracting absorbance reading of the assay when homogenization buffer was used instead of brain homogenate. Any negative net absorbance was reported as zero. The upper limit of the Quantum Spectrophotometer used was 2.0 absorbance. An absorbance over this limit was reported as 2.0. Serial dilution indicated absorbance equivalence of up to 16 were sometimes obtained. The data was analyzed using a Student-t test and Spearman rank correlation coefficient.

The clinical data, patient information, pathological reports, and Alzheimer antigen assay results for the 111 cases studied are summarized below in Table 4. Generally, the AD cases were older than NC cases (75.8 vs 60.7 years), but NDC cases were comparable to AD group (69.8 vs. 75.8). Considering only cases that were 65 or older, the average ages becomes comparable, 74.4, 76.7, and 78.8 years for NC, NDC, and AD categories respectively. D/AD cases were all older than 50 (average age, 53). Post mortem time varied from as short as 1 hour to as long as 96; some cases did not have this information available. Pathological reports indicated that all specimens in the AD group (AD, SDAT, and D/AD categories) contained plaques ranging from mild to severe, but mostly severe. With respect to the severity of plaques in the non-AD group, NC cases had fewest plaques in the fewest cases, while NDC specimens had a reported density between NC and AD. Generally, the plaques were not classified as neuritic or diffuse in nature. All of the cases in the AD group were clinically demented, whereas none of the cases in the NC category were observed to have dementia. The majority of NDC cases were classified as demented.

TABLE 4

SUMMARY OF CLINICO-PATHOLOGICAL DATA AND ALZHEIMER ANTIGEN CONCENTRATIONS

| Parameters Reported or Measured | Non-AD Group NDC | Non-AD Group DC |
|---|---|---|
| Number of Samples (n) | 27 | 28 |
| Alzheimer Antigen Immunoreactivity (Absorbance/10 mg)* | 0.01 (0.0–0.08) | 0.01 (0.0–0.06) |
| Mean Age (range) | 60.7 (35–84) | 69.8 (40–90) |
| Post Mortem Time (hours.)** | 2–64 | 1–80 |
| Number of Cases 65 and Older | 11 | 11 |
| Mean Age for Cases 65 and Older | 74.4 | 76.7 |
| Immunoreactivity for Cases 65 and Older* | 0.01 (0.0–0.02) | 0.01 (0.0–0.04) |
| SEVERITY OF Plaques (N): | | |
| No Plaques | 22 | 12 |
| Mild | 4 | 8 |
| Moderate | 1 | 6 |
| Severe | 0 | 2 |
| Number of Clinically Demented | 0/27 | 16/28 |
| Number in which Alzheimer Antigen is present | 0/27 | 0/28 |

| Parameters Reported or Measured | AD Group AD | AD Group SDAT | D/AD |
|---|---|---|---|
| Number of Samples (n) | 46 | 7 | 3 |
| Alzheimer Antigen Immunoreactivity (Absorbance/10 mg)* | 1.39 (0.03–2.0) | 0.01 (0.0–0.64) | 2.0 (0.70–2.0) |
| Mean Age (range) | 75.8 (46–92) | 77 (71–85) | 53 (52–55) |
| Post Mortem Time (hours.)** | 1.5–96 | 1.5–12 | 18.5–46 |
| Number of Cases 65 and Older | 40 | 7 | 0 |
| Mean Age for Cases 65 and Older | 78.8 | 77 | — |
| Immunoreactivity for Cases 65 and Older* | 0.85 (0.03–2.0) | 0.01 (0.0–0.64) | — |
| SEVERITY OF Plaques (N): | | | |
| No plaques | 0 | 0 | 0 |
| Mild | 1 | 2 | 0 |
| Moderate | 5 | 3 | 0 |
| Severe | 40 | 2 | 3 |
| Number of Clinically Demented | 46/46 | 7/7 | 1/3 |
| Number in which Alzheimer Antigen is present | 43/46 | 2/7 | 3/3 |

NC: Normal Control; NDC: Neurological Disease Control;
AD: Alzheimer's disease; SDAT: Senile Dementia of Alzheimer's Type;
D/AD: Down's with AD histopathology
*Median (range)
**Not available for every case The Alzheimer's disease group had significant Alzheimer antigen concentrations (expressed as per protein or per 10 mg of tissue weight), which is in contrast to both the normal and other neurological disease groups. The normal brain group and the group of other neurological diseases essentially had no detectable Alzheimer antigens. The Alzheimer antigen concentrations in AD category had a median of 1.39 and ranged from 0.03 to 2.0 absorbance/10 mg tissue. The D/AD category mimicked AD, but the SDAT category demonstrated a wide range of the Alzheimer antigen concentrations (from 0 to 0.64). The Alzheimer antigen levels in NC and NDC categories were not significantly different (Student-t test, p>0.797). In contrast, Alzheimer antigen level in the AD Group (n=56) was higher than non-AD group (n=55) using Student-t test (p <0.0005). When the Alzheimer antigen concentrations in various categories were recalculated using cases 65 and older, the maximum values were actually reduced. The AD group had an overall median of 0.77 and ranged from 0.0 to 2.0 absorbance units per 10 mg. tissue.

FIG. 5 represents a scattergram plot of the Alzheimer antigen concentration for the AD/SDAT versus the combined normal and other neurological group at two different scales. The group of normal brains and the group of other neurological diseases are presented together in FIG. 5 due to the lack of difference in the Alzheimer antigen concentrations (Dunnet's Test, p 0.05). An absorbance value of 0.1 was used as an empirically derived cut off between Normal range and AD range. Alzheimer antigen concentrations for all non-AD cases fell under this line whereas Alzheimer antigen concentrations for 48 out of 56 cases in AD group fell above this line. Only three cases in AD category overlapped with NC and NDC cases. It is noteworthy that there was no increase in Alzheimer antigen levels in NDC category even though dementia was observed in 16 of a total of 28 cases. D/AD category also had Alzheimer antigen levels comparable to AD, but SDAT cases had Alzheimer antigen concentrations in both Normal range and AD range.

The data also was analyzed by a stepwise multiple regression analysis with forward selection technique (using dummy variables for diagnosis, gender, and pathological findings) and by Dunnet's Test when comparing the AD/SDAT and the other neurological diseases groups' Alzheimer antigen levels to those of the normal group. The regression analysis considered the variables for diagnosis, age, sex, post-mortem delay and pathological report and explained the variance of the Alzheimer antigen concentration (separate statistical analysis for each Alzheimer antigen concentration unit category). The two dependent variables were Alzheimer antigen concentration expressed as absorbance/mg protein and as absorbance/10 mg wet tissue. Fifteen percent (15%) of the variation of the former and 39% of the latter was explained (p=0.0001) by the diagnosis category alone. The variation was further explained by considering the neurofibrillary tangles and plaque counts to the extent of 7 and 5% (p 0.01), respectively. Finally, age was found to contribute 4 and 3%, respectively, to each variation but was inversely correlated (p 0.05). Thus, the total correlation coefficient (R2) was found to be 26 and 46%, respectively.

Figure 5A:
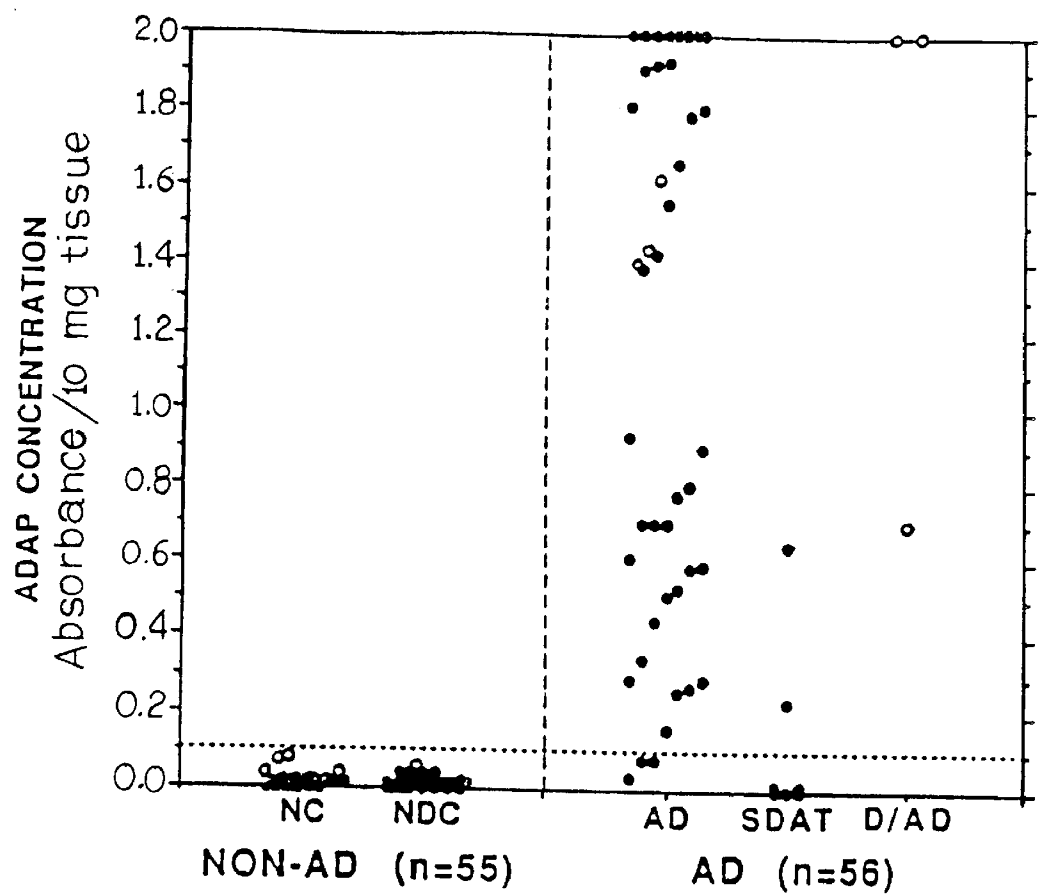
FIG. 5A represents a full scale graph scattergram plot of the Alzheimer antigen or concentrations for each diagnostic category: NC=Normal Control: NDC=Neurological Disease Control: AD=Alzheimer's Disease: SDAT=Senile Dimentia of Alzheimer's Type: D/AD=Down's Syndrome with AD Neurohistology; Non-AD group includes NC and NDC, and AD group includes AD, SDAT and D/AD. Closed circles are values for 65 and older cases, open circles are values for under 65 cases. The circles on the 2.0 line are either 2.0 or higher (up to 16)
Figure 5B:
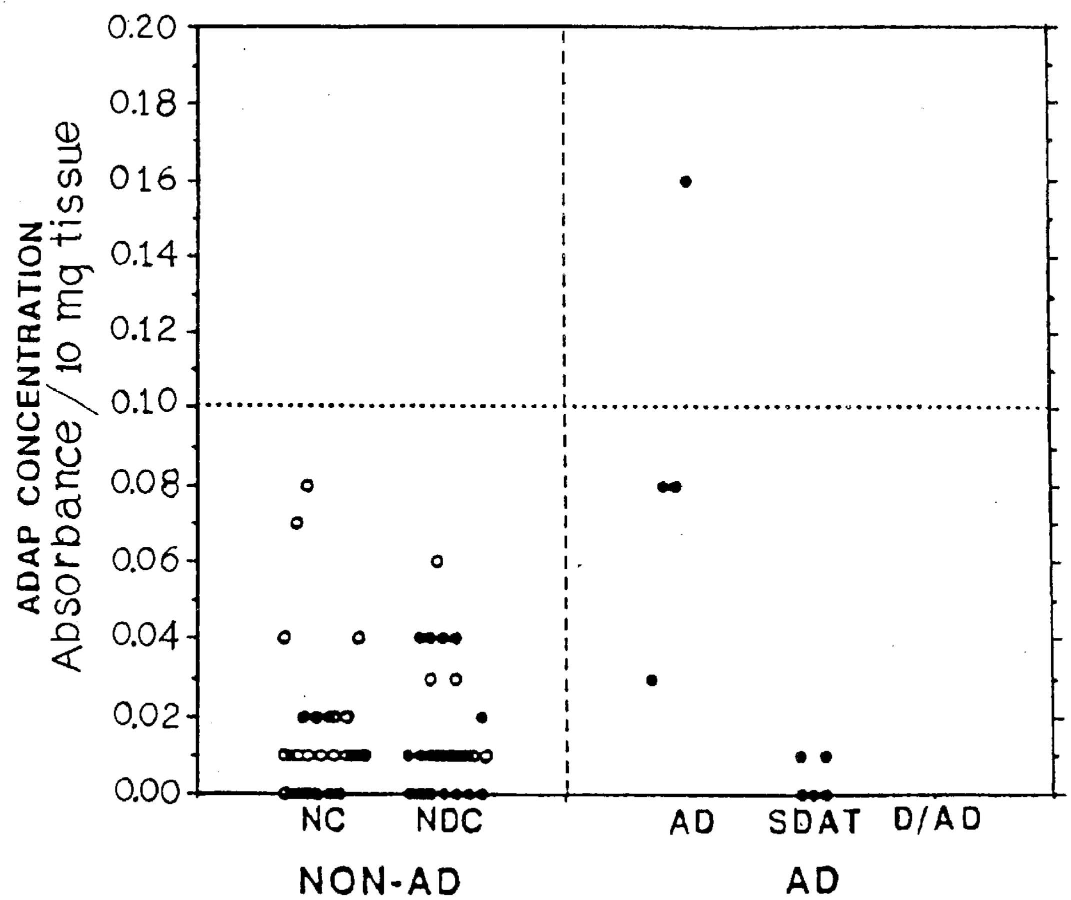
FIG. 5B represents a y-axis 10 fold expansion of FIG. 4A.

While Alzheimer's disease is associated with dementia, neuritic plaques and aging, dementia alone was not associated with an increase in Alzheimer antigen concentration, as there were 24 demented cases (16 NDC's, 3 AD's, 5 SDAT's) in the normal range for Alzheimer antigen (Table 4 and FIGS. 5A and 5B). Furthermore, plaques were not always associated with the presence of Alzheimer antigen since some of them were probably diffuse plaques lacking the dystrophic neurites containing Alzheimer antigen. There were 29 cases (5NC's, 16NDC's, 3AD's, 5 SDAT's) with plaques which had practically no detectable Alzheimer antigen levels (see Table 4, and FIGS. 5A and 5B).

To examine the concentration of Alzheimer antigen as a function of age, the data pertaining to Alzheimer antigen concentrations were recalculated for the 65 and older cases. Based on this anaylsis, the maximum value of Alzheimer antigen in 65 and older cases was actually lower in NC and NDC categories, and the median in AD category was decreased from 1.39 to only 0.85 for 65 and older cases (see Table 4). Furthermore, in FIGS. 5A and 5B, the Alzheimer antigen concentrations for 65 and older cases are presented in filled circles and for under 65 cases in open circles. There is no age related pattern apparent in the Figures. The highest values of Alzheimer antigen immunreactivity in both NC and NDC categories correspond to cases under 65 (open circles, FIGS. 5A and 5B). The Spearman Correlation Test showed a 15% (not significant) probability of Alzheimer antigen concentration being negatively correlated with age. The oldest NDC case was a 90 year old female with multi-infarct dementia showing moderate plaques, and yet with Alzheimer antigen concentration of 0.01 absorbance unit/10 mg tissue, while the youngest AD case was 46 years old and had an Alzheimer antigen concentration of more than 2.0.

It is apparent from the data that the claimed immunoassay distinguishes AD/SDAT from both normal and other neurological diseases. Furthermore, based on this data, clinical dementia, plaques, and old age per se do not appear to be associated with the increased Alzheimer antigen levels in the AD group. Thus, using this assay, regional variations can be examined, as well as the relationship of the Alzheimer antigen concentration to duration of the disease.

EXAMPLE 7

Brain Tissue Extract Assays Utilizing Monoclonal Antibodies

The following diagnostic assay employs monoclonal antibodies as both the first and second antibodies. The first antibody is referred to as the capture antibody, and the second antibody is referred to as the detection antibody. Various combinations of capture antibodies and detection antibodies were utilized. As shown in FIGS. 7A–7M, both Alzheimer's disease brain extract and normal brain extract were utilized with the various antibody combinations. The brain extracts were obtained as described herein.

For FIGS. 7A–7M, the Y axis represents optical density, and shows the level of Alzheimer's disease antigen in the brain tissue extracts. The X axis indicates the amount of brain protein used in the assay in nanograms.

In all of the assays performed, no significant level of Alzheimer's antigen was detected in normal brain. However, in every assay performed on Alzheimer's disease brain, Alzheimer's antigen was detected. Hence, the monoclonal antibodies of the invention can be used in various combinations to produce sensitive and specific assays which detect the presence of Alzheimer's antigen, and thereby diagnose Alzheimer's disease.

EXAMPLE 8

Diagnostic Assay for Alzheimer's Antigen in Cerebrospinal Fluid

Protocol A

Detection of the Alzheimer antigen in cerebrospinal fluid (CSF) was performed using a modified Western blot protocol. Alzheimer's disease antigen was precipitated from 3.5 ml CSF by addition of an equal volume of saturated ammonium sulfate (SAS) and incubating for 30 minutes at 40° C. The solution was then centrifuged at 5000 g and the pellet was dissolved in 40 ml of 0.01M sodium phosphate and dialyzed into PBS pH 7.4 overnight. The sample was dissolved in 5% SDS-5% beta-mercaptoethanol, fractionated on a 10% SDS-polyacrylamide gel, and transferred to nitrocellulose. The nitrocellulose was incubated for 1 hr in PBS pH 7.4 plus 5% nonfat dry milk and 1% human serum. Overnight incubations with Alzheimer antibody followed by a 3 hour incubation with peroxidase coupled goat antimouse antibody both diluted in blocking solution containing 1% human serum was performed. Presence of peroxidase was visualized by reacting with 4-chloro-1-naphthol (0.2 mg/ml) plus 0.44 mM hydrogen peroxide in 0.1M Tris pH 4.5.

Alzheimer antigen was readily detected in CSF. The nine CSF samples examined were obtained by lumbar puncture from presumptive Alzheimer patients and one CSF sample obtained by cisternal magna puncture obtained from a deceased patient whose diagnosis of Alzheimer's disease was later confirmed by neuropathologic analysis. Eight of the nine samples from the living patients and one sample from the deceased patient yielded a Western blot pattern showing the characteristic 68,000 dalton doublet.

CSF was also obtained by lumbar puncture from 6 non-demented patients. These samples did not show the 68,000 dalton doublet. In addition, a CSF sample was examined from one patient who died with an initial clinical diagnosis of Alzheimer's disease. Western blot analysis of the CSF did not reveal a 68,000 dalton doublet. Subsequent analysis by neuropathology showed no neuritic plaque or neurofibrillary tangle pathology indicating that the patient did not die from Alzheimer's disease.

All samples examined, presumptive Alzheimer and nondemented, exhibited variable amounts of staining of proteins in the 20,000–50,000 dalton molecular weight range that did not correlate with presence of dementia. Hence, the staining of these smaller proteins is of no diagnostic value.

This example shows that the high degree of accumulation of Alzheimer antigen and the high degree of Alzheimer antibody immunoreactivity is unique to Alzheimer's disease. Quantitation by ELISA shows that under conditions favoring high affinity antibody binding, there was 56 times more Alzheimer antibody immunoreactivity present in brains of Alzheimer's disease patients than in brains of normal patients, and that there was 33 times more Alzheimer antibody immunoreactivity in brains from Alzheimer cases than in brains from cases with Pick's Disease or GPD. Immunocytochemistry suggested that this increased reactivity is largely the result of the abundant reactivity of abnormal neurites present in brains affected by Alzheimer's disease. Other diseases possess very little abnormal neuritic reactivity. The selective increase in neuritic reactivity in Alzheimer's disease explains the specificity of plaque staining by Alzheimer antibody. Only in Alzheimer's disease does Alzheimer antibody immunoreactivity extend from the affected cell body into the neurites and into the neuritic plaques.

Different values have been obtained indicating the differential between Alzheimer antigen immunoreactivity in Alzheimer's Disease brain samples when compared to other neurologic diseases or age-matched controls. Table 1 indicates a 7–8 fold difference, while in this example, the difference between Alzheimer's Disease and controls is stated to be, on average, 56 times whereas the difference between Alzheimer's Disease in comparison to Pick's Disease and GPD is 33 fold higher. There are two reasons for these discrepancies. First, different assay configurations can result in the capture of more Alzheimer antigen depending on the specific Alzheimer antibodies used and the mechanism of capture (e.g., a dry-down direct assay vs. a true dual antibody capture-detection protocol). Second, the amounts of Alzheimer antigen in controls is often zero. Better antibodies or assay configurations resulting in lower backgrounds will lead to larger differentials between Alzheimer Disease and control brain extracts.

Protocol B

Alzheimer antigen is precipitated from 3.5 ml of cerebrospinal fluid by incubation with an equal volume of saturated aqueous ammonium sulfate at 4° C. The samples are spun in a centrifuge at about 20,000 g for about 20 minutes at 4° C. The supernatant is removed and the pellet is broken up in 50 microliters of aqueous 0.01M sodium phosphate at pH 6.8. Western blot analysis is used to detect the Alzheimer antigen. The samples are run on a 10 percent SDS-PAGE gel. The Alzheimer antigen is transferred to nitrocellulose for three hours at 125 mA and the buffer contains 19.2 mM glycine, 2.5 mM trizma base and 20 percent methanol at pH 8.3. Successive treatments are carried out with a blocking solution of 0.01M TBS with 5% v/w dried milk at pH 7.4 for one hour and then Alzheimer antibodies and the blocking solution for one hour.

Thereafter, five 5 minute washes are carried out. A phosphatase or peroxidase-coupled goat anti-mouse antibody and the blocking solution plus 1% human serum is used for one hour followed by another five 5 minute wash. Color development is achieved by use of a commercially available composition BCIP/NBT (Kirkegaard & Perry) or 4-chloronaphthol. The color develops over night. Tests on the cerebrospinal fluid of three Alzheimer patients was positive for each test. A test carried out on the cerebrospinal fluid from a neurologically normal person did not show the presence of the Alzheimer antigen.

Protocol C

Cerebrospinal Fluid Assays Utilizing Monoclonal Antibodies

Alzheimer's disease antigen was concentrated from cerebrospinal fluid by immunoaffinity chromatography. Cultures of the ALZ-50 cell line were screened to isolate an IgGl secreting variant. Class-switch variants arose spontaneously in cultures of IgM secreting cells. The variant was designated P42, and was shown to retain the ALZ-50 binding properties using ELISA, Western blotting and immunocytochemistry. The P42 IgGl was purified by chromatography on protein A columns, and attached to Affi-gel 10 (Biorad Laboratories) following the manufacturers protocol. Columns were prepared on P42 Affi-gel 10. Cerebrospinal fluid from cases of Alzheimer's disease and from non-demented individuals was run through the column, and the column was then washed with Tris-buffered saline. Bound antigens were eluted with a solution of 3M potassium thiocynate. When cerebrospinal fluid from cases of Alzheimer's disease was used, small quantities of protein (less than 1 microgram per ml of fluid used) was detected in the eluate. No detectable protein was eluted from columns used with cerebrospinal fluid from non-demented individuals.

Western blot and ELISA assays using monoclonal antibodies Alz-50, TG3 and analyses on fractions from columns using cerebrospinal fluid from non-demented individuals did not reveal any immunoreactive proteins. Hence, cerebrospinal fluid can be concentrated prior to being utilized in the assay of the invention. However, it is not necessary to concentrate cerebrospinal fluid prior to utilizing it in the assay of the invention.

Cerebrospinal fluid from both normal and Alzheimer's disease individuals was assayed for the presence of Alzheimer's antigen on a solid support, as described herein, in order to diagnose Alzheimer's disease. Monoclonal antibody TG5 was used as the first antibody to capture the Alzheimer's antigen in cerebrospinal fluid. Monoclonal antibody MC15 was used to detect the captured antigens. No concentration of cerebrospinal fluid was employed for this assay.

Figure 8:
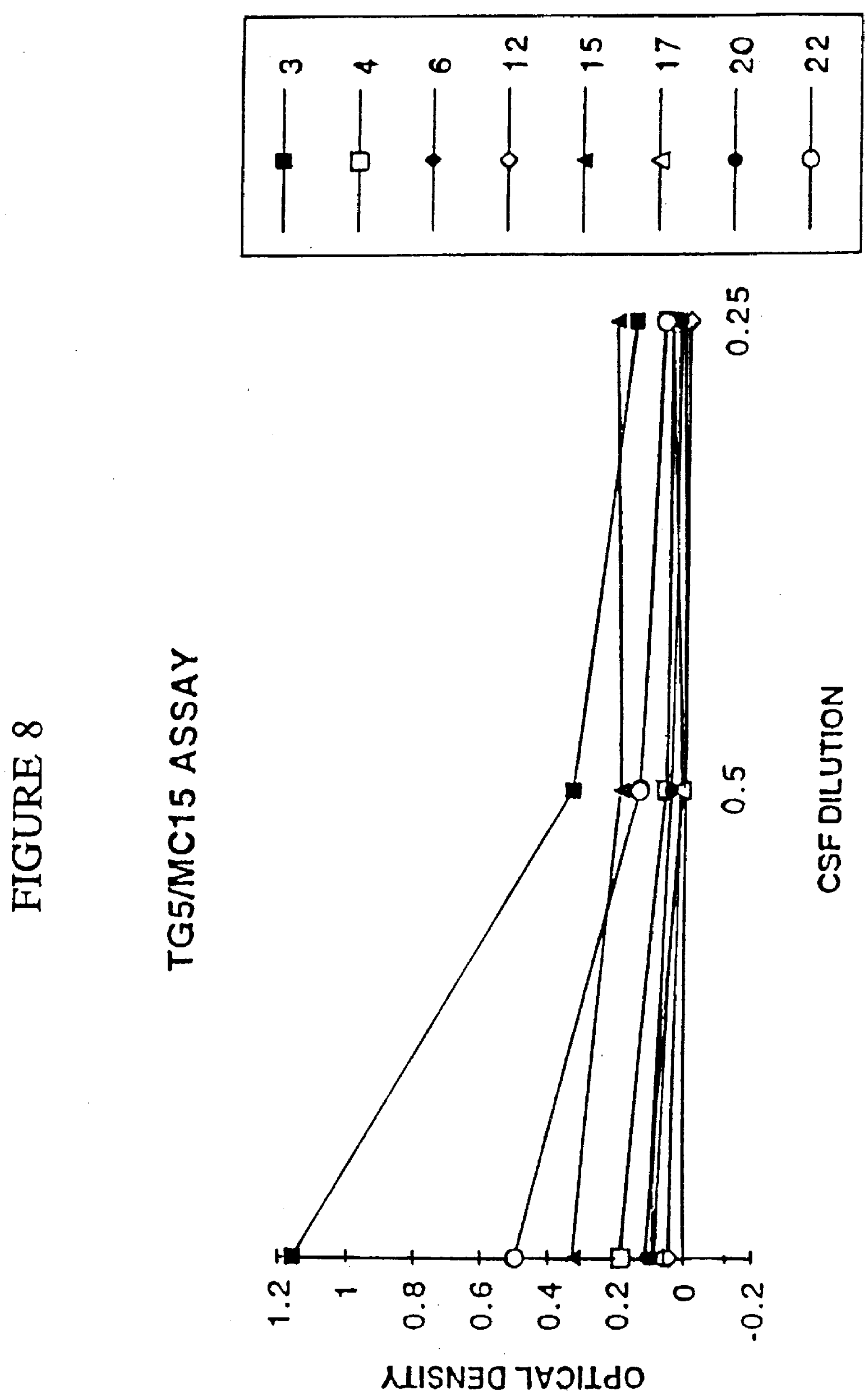
FIG. 8 represents a cerebrospinal fluid assay for determining the presence of Alzheimer's antigen in both Alzheimer's disease individuals and normal individuals wherein the captured monoclonal antibody is TG5 and the detection is antibody is MC15.

The samples were obtained from individuals at the time of autopsy, which allowed the diagnosis of the precise nature of each individual's condition. Sample numbers 3, 4, 15 and 22 were from individuals who had Alzheimer's disease, and sample numbers 6, 12, 17 and 20 were derived from normal individuals. As shown in FIG. 8, only those samples that were from individuals with Alzheimer's disease had significant levels of Alzheimer's antigen present.

Figure 9:
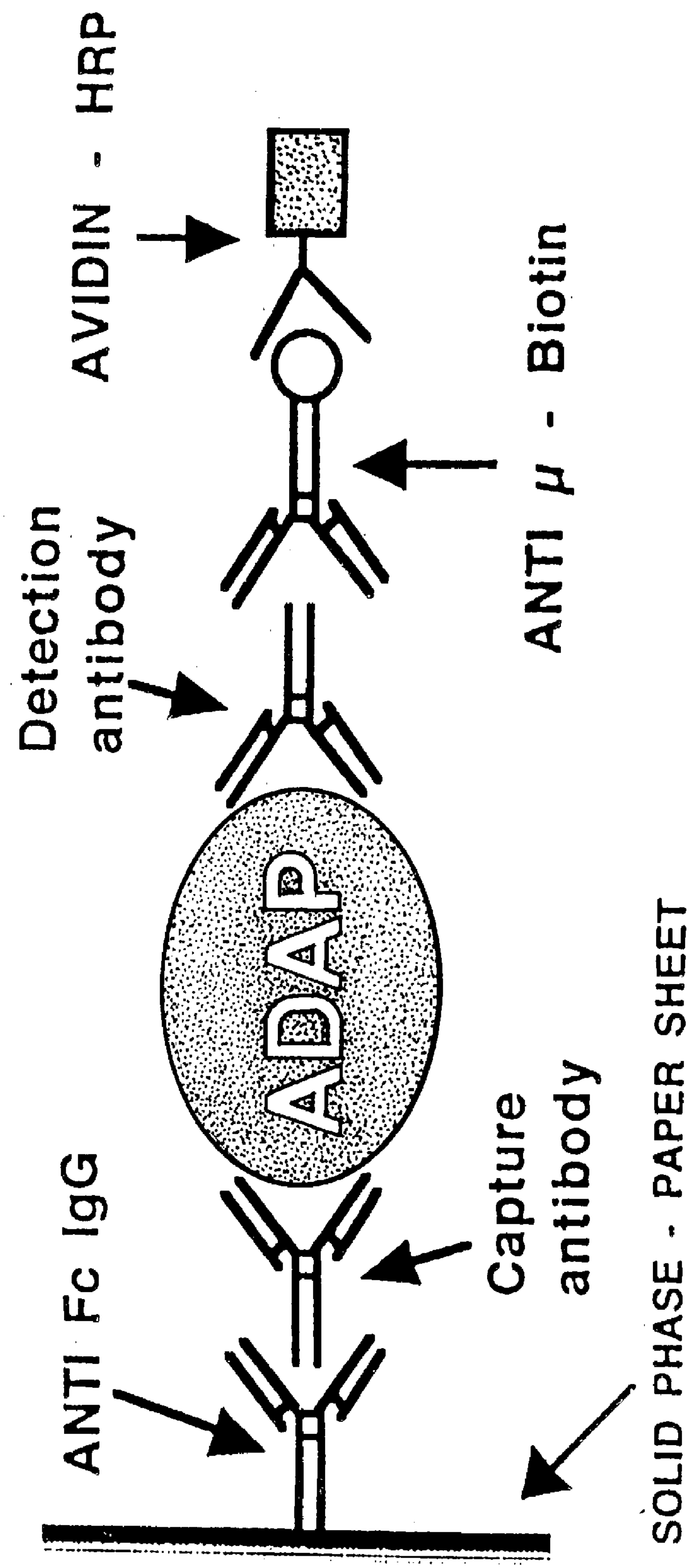
FIG. 9 represents an assay of the invention for detecting Alzheimer's antigen wherein the capture antibody is on a solid phase.

Immobilized ALZ-50 can also be used to detect the presence of Alzheimer's antigen in cerebrospinal fluid, thereby diagnosing Alzheimer's disease. This method can also be used to detect Alzheimer's antigen in extracts of human brain (homogenization of brain in TRIS methods). As shown in FIG. 9, the assay can be built out from several solid phases (i.e., nitrocellulose or PVDF paper). The first antibody is an anti-Fc IgG specific antibody which is noncovalently bound to the paper. Next, the uncovered sites on the paper are blocked with a variety of blocking agents; e.g., BSA, casein, gelatin. The capture antibody is then added, and the sample is allowed to bind to the paper. Next, the detection antibody is added. An anti-$\mu$ chain specific biotinylated antibody is added, and an avidin HRP conjugate is added. The substrate used can be any of several, including ECL, ABTS and TMB. The presence of Alzheimer's antigen is then determined, the presence of said antigen correlating with a positive diagnosis of Alzheimer's disease.

Figure 10:
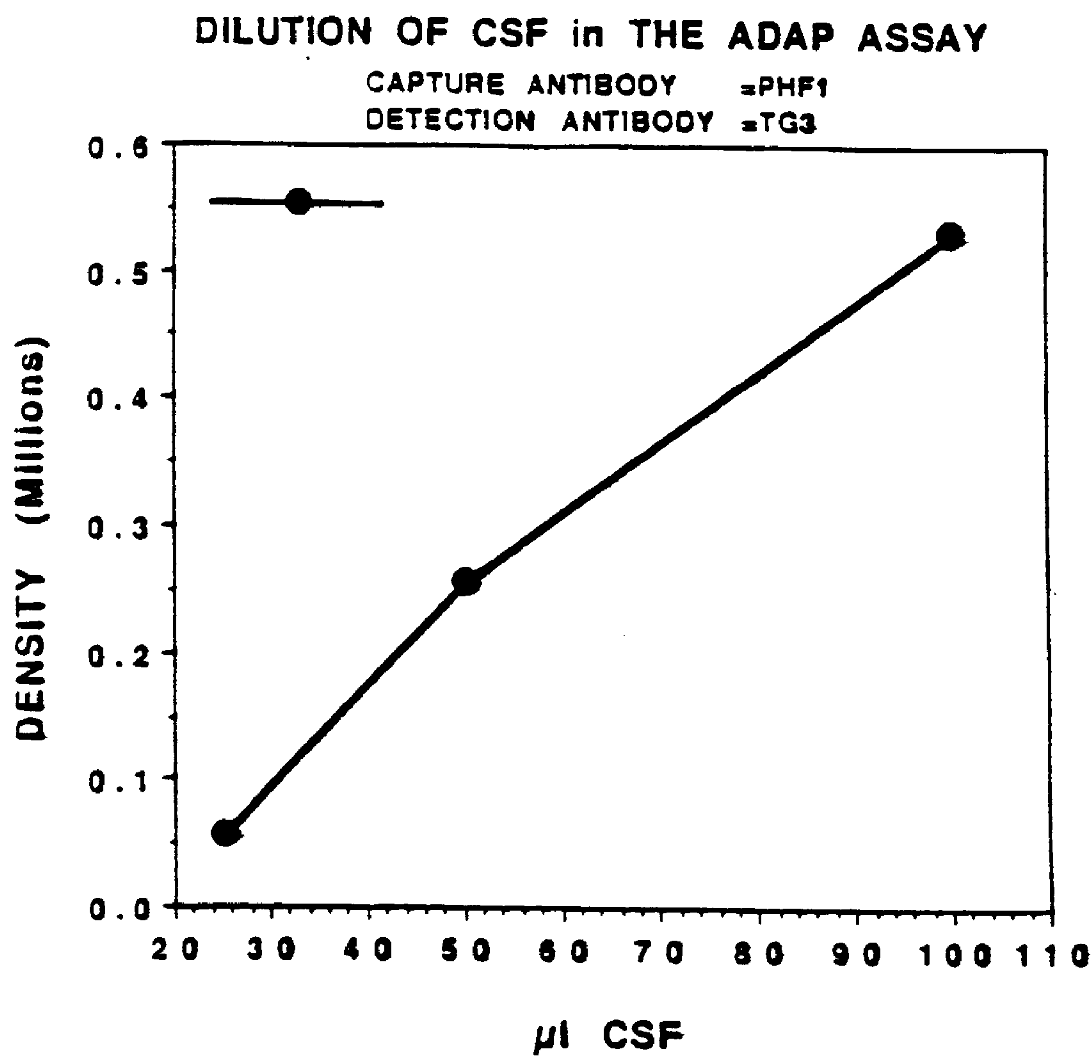
FIG. 10 represents a cerebrospinal fluid assay for the detection of Alzheimer's antigen wherein the capture antibody is PHF-1 and the detection antibody is TG3.

In a preferred embodiment of the invention, the capture monoclonal antibody is of the IgG isotype, and is selected from the group consisting of PHF-1, TG5 and MC1. The detection monoclonal antibody is of the IgM isotype, and is selected from the group consisting of TG3, TG4 and MC15. FIG. 10 shows a CSF assay which indicates that Alzheimer's disease antigen is present, wherein the capture antibody used in the assay is PHF-1, and the detection antibody used in the assay is TG3.

Protocol D

Cerebrospinal Fluid Assay Utilizing Monoclonal and Polyclonal Antibodies

Alzheimer's antigens can be detected in cerebrospinal fluid utilizing both polyclonal and monoclonal antibodies in the assay of the invention. Polyclonal antibody was used to capture the Alzheimer antigens, and monoclonal antibody PHF-1 was used to detect the bound antibodies. No concentration of cerebrospinal fluid was employed for this assay. Cerebrospinal fluid samples were obtained from individuals visiting clinics specializing in the diagnosis and treatment of memory disorders. Approximately 140 samples were tested, and individuals were grouped according to accepted standards of clinical diagnosis. The individuals were grouped as follows:

AD-1: These individuals met the best available clinical criteria for the diagnosis of Alzheimer's disease, and are generally described as probably AD. When such a diagnosis is made by one skilled in the art, about 90% of these patients would be found on autopsy to have Alzheimer's disease.

AD-2: These individuals met most, but not all, of the generally accepted criteria for diagnosis of Alzheimer's disease. Because of certain atypical features, they are described as possible AD, and 75% to 85% of these individuals would be found at autopsy to have suffered from Alzheimer's disease.

PC: These individuals were diagnosed as suffering from one or more psychiatric disorders, such as depression, manic-depressive illness or schizophrenia.

NC: These individuals were diagnosed as being free from dementia at the time of examination, and are considered to be normal controls. Two individuals in this group had somewhat increased levels of immunoreactivity. Both patients were elderly women with some impairment of cognitive function; however, this impairment was insufficient to warrant a diagnosis of dementia.

NDC: This group of individuals was diagnosed as having a neurologic disorder other than Alzheimer's disease. Included in this group are individuals with Parkinson's disease, Huntington's Chorea or multi-infarct dementia.

MIX: The clinical diagnosis in this group of individuals suggested the presence of more than one neurologic condition, the majority of the individuals having a combination of Alzheimer's disease, multi-infarct dementia and/or Parkinson's disease.

Figure 11:
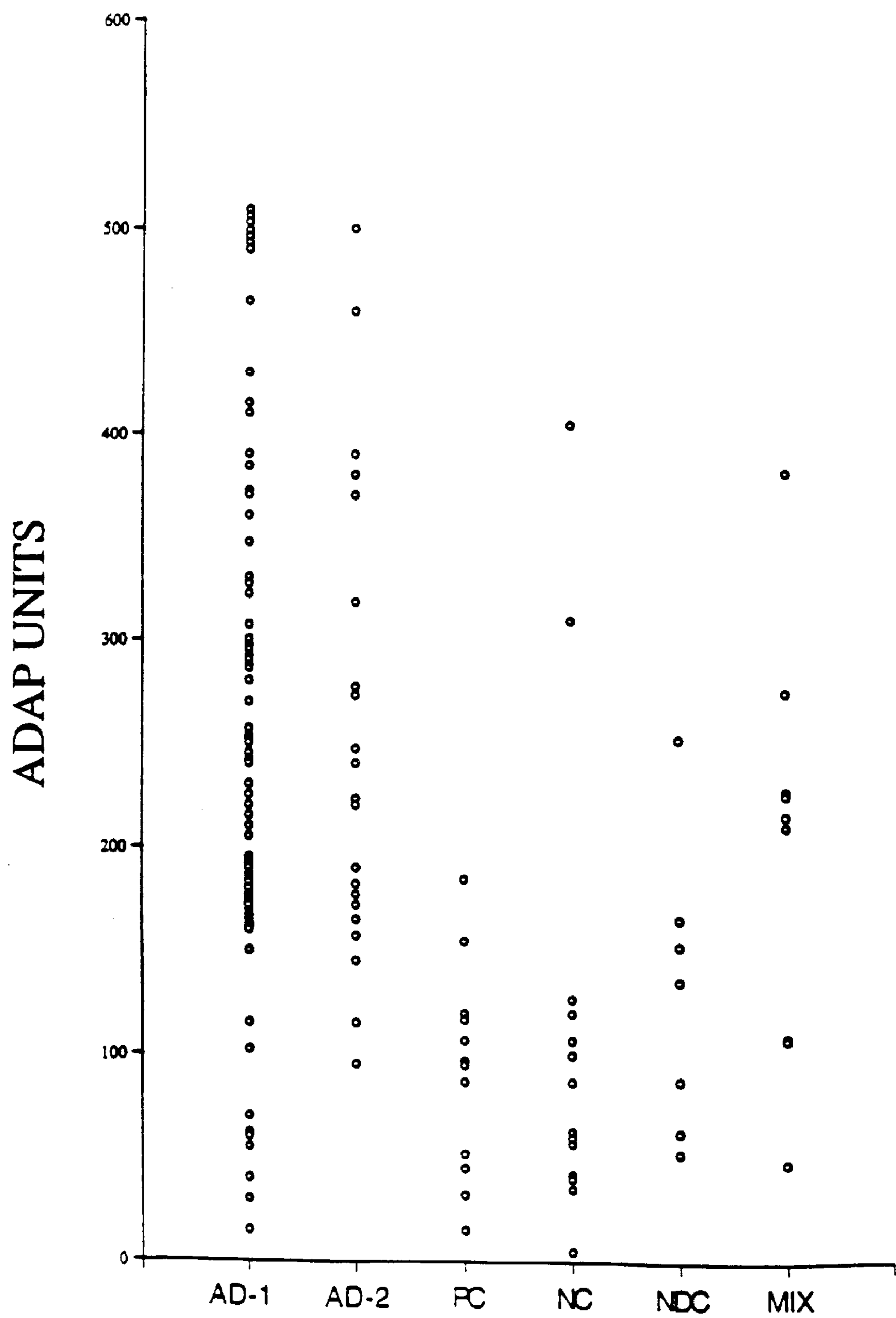
FIG. 11 represents levels of Alzheimer's antigen in various individuals utilizing a cerebrospinal fluid assay and both monoclonal and polyclonal antibodies.

As shown in FIG. 11, the great majority of individuals with probable or possible Alzheimer's disease had high levels of antibody immunoreactivity with Alzheimer's antigen. In contrast, normal controls and individuals with other diseases did not show increased levels of Alzheimer's antigen immunoreactivity. Hence, polyclonal and monoclonal antibodies can be used in a cerebrospinal fluid assay of the invention to detect the presence of Alzheimer's antigen, thereby positively diagnosing Alzheimer's disease.

All documents, e.g. publications and patents, referenced hereinabove are incorporated by reference in their entirety.

The above descriptions, features and advantages of the present invention are set forth to aid in an understanding of the present invention but are not intended, and should not be construed, to limit the invention as defined by the claims which follow hereafter.

What is claimed is:

1. A hybridoma cell line identified as ATCC No. HB 9205.

2. A monoclonal antibody produced by a hybridoma cell line of claim 1.

3. A method for determining Alzheimer's disease in an individual comprising:

a. contacting a sample obtained from the individual with an antibody immunologically reactive with a first antigenic determinant found in brain tissue of individuals having Alzheimer's disease such that a first antibody-antigen complex is formed, where the antibody is secreted by a hybridoma cell line identified as ATCC No. HB 9205;

b. measuring the amount of the complex; and c. comparing the amount of the complex in the sample with the amount in a control wherein an elevated level of the complex in the sample indicates the individual has Alzheimer's disease.

4. A method of claim 3, wherein the sample is selected from cerebrospinal fluid, brain tissue extract, urine and blood.

5. A method of claim 4, wherein the antibody is attached to a solid matrix.

* * * * *